(12) United States Patent
Williams

(10) Patent No.: US 8,501,695 B2
(45) Date of Patent: Aug. 6, 2013

(54) TISSUE KALLIKREIN FOR THE TREATMENT OF DISEASES ASSOCIATED WITH AMYLOID PROTEIN

(75) Inventor: Mark Williams, Winnipeg (CA)

(73) Assignee: DiaMedica, Inc., Winnipeg, Manitoba (CA)

( * ) Notice: Subject to any disclaimer, the term of this patent is extended or adjusted under 35 U.S.C. 154(b) by 358 days.

(21) Appl. No.: 12/669,776

(22) PCT Filed: Jul. 18, 2008

(86) PCT No.: PCT/CA2008/001327
§ 371 (c)(1),
(2), (4) Date: May 13, 2010

(87) PCT Pub. No.: WO2009/012571
PCT Pub. Date: Jan. 29, 2009

(65) Prior Publication Data
US 2010/0226910 A1    Sep. 9, 2010

Related U.S. Application Data

(60) Provisional application No. 60/950,960, filed on Jul. 20, 2007, provisional application No. 61/023,505, filed on Jan. 25, 2008, provisional application No. 61/056,411, filed on May 27, 2008, provisional application No. 61/061,322, filed on Jun. 13, 2008.

(51) Int. Cl.
*A61K 38/00* (2006.01)
*A61K 38/43* (2006.01)
*A61K 38/48* (2006.01)
*C12N 9/00* (2006.01)
*C12N 9/48* (2006.01)
*C12N 9/50* (2006.01)

(52) U.S. Cl.
USPC ....... 514/17.8; 424/94.64; 435/183; 435/212; 435/219; 514/17.7

(58) Field of Classification Search
None
See application file for complete search history.

(56) References Cited

U.S. PATENT DOCUMENTS

| 5,534,615 | A | 7/1996 | Baker et al. | |
|---|---|---|---|---|
| 6,288,040 | B1 * | 9/2001 | Muller et al. | 514/1.2 |

(Continued)

FOREIGN PATENT DOCUMENTS

| WO | WO 01/56532 | 8/2001 |
|---|---|---|
| WO | WO 2004/058258 | 7/2004 |

(Continued)

OTHER PUBLICATIONS

Chao 2006 "Experimental therapy with tissue kallikrein against cerebral ischemia" Frontiers in Bioscience 11.*
Sun 2004 "Prolonged hypotensice effect of human tissue kallikrein gene delivery and recombinant enzyme administration in spontaneous hypertension rats" Exp Mol Medicine 36:1.*

(Continued)

*Primary Examiner* — Jeffrey Stucker
*Assistant Examiner* — Adam M Weidner

(57) ABSTRACT

This invention relates to methods of treating Alzheimer's disease or symptoms thereof, and amnesic mild cognitive impairment or symptoms thereof. Methods of the invention include administering a therapeutically effective amount of tissue kallikrein, variants or active fragments thereof. The invention further relates to uses of tissue kallikrein or a variant or active fragment thereof for the digesting or cleaving amyloid and the treatment of conditions benefiting from the digestion or cleavage of amyloid. The invention further relates to pharmaceutical compositions comprising a therapeutically effective amount of tissue kallikrein, variants or active fragments thereof formulated for oral or intranasal administration.

13 Claims, 10 Drawing Sheets

C20408 LDH
Kallikrein Study Arm A,B and C

*** $p<0.0001$ (1-way ANOVA) ) represents statistically significant difference compared to the vehicle (=10μM $A\beta_{1-42}$) group.

U.S. PATENT DOCUMENTS

| | | | |
|---|---|---|---|
| 6,962,793 B2 | 11/2005 | Diamandis | |
| 7,195,759 B2* | 3/2007 | Sabbadini et al. | 424/94.64 |
| 2007/0224209 A1* | 9/2007 | Berczi et al. | 424/184.1 |
| 2009/0162342 A1* | 6/2009 | Berczi et al. | 424/94.64 |
| 2009/0233995 A1* | 9/2009 | Lautt | 514/440 |
| 2010/0008899 A1* | 1/2010 | Williams | 424/94.64 |
| 2011/0150781 A1* | 6/2011 | Charles et al. | 424/43 |
| 2012/0070425 A1* | 3/2012 | Williams et al. | 424/94.64 |
| 2012/0201804 A1* | 8/2012 | Williams et al. | 424/94.64 |
| 2012/0225051 A1* | 9/2012 | Williams et al. | 424/94.64 |

FOREIGN PATENT DOCUMENTS

| | | |
|---|---|---|
| WO | WO 2005/022146 | 3/2005 |
| WO | WO 2005/022164 | 3/2005 |
| WO | WO 2006/008002 | 1/2006 |
| WO | WO 2008/011713 | 1/2008 |
| WO | WO 2010/009557 | 1/2010 |
| WO | WO 2010/108262 | 9/2010 |
| WO | WO 2010/121358 | 10/2010 |
| WO | WO 2010/121361 | 10/2010 |
| WO | WO 2012/075342 | 6/2012 |
| WO | WO 2012/154574 | 11/2012 |

OTHER PUBLICATIONS

Turner 2004 "Targeting Amyloid-degrading Enzymes as Therapeutic Strategies in Neurodegeneration" Ann NY Acad Sci 1035.*

Vickers 2002 "A vaccine against Alzheimer's disease" Drugs Aging 19:7.*

Little et al., "Zyme, a novel and potentially amyloid ogenic enzyme cDNA isolated from Alzheimer's disease brain," *The Journal of Biological Chemistry* (1997) 272 (40): 25135-25142.

Klafki et al., "Therapeutic approaches to Alzheimer's disease," *Brain* (2006) 129: 2840-2855.

Form PCT/IB/373 for International Application PCT/CA2008/001327.

Born et al., "Sniffing neuropeptides: a transnasal approach to the human brain," *Nature Neuroscience* (2002) 5 (6): 514-516.

Buckner et al., "Molecular, structural, and functional characterization of Alzheimer's disease: Evidence for a relationship between default activity, amyloid, and memory," *The Journal of Neuroscience* (2005) 25 (34): 7709-7717.

Castro et al., "Does the Kunitz domain from the Alzheimer's amyloid β protein precursor inhibit a kallikrein responsible for post-translational processing of nerve growth factor precursor," *FEBS Lett.* (1990) 267 (2): 207-212.

Diamandis et al., "Human Kallikrein 6 as a Biomarker of Alzheimer's Disease," *Clin. Biochem.* (2000) 33: 663-667.

Editorial, "Neuropathology of amnestic mild cognitive impairment," *Arch. Neurol.* (2006) 63: 645-646.

Frank et al., "A review of antioxidants and Alzheimer's Disease," *Annals of Clinical Psychiatry* (2005) 17 (4): 269-286.

Friedlander et al., "Alzheimer's disease: Psychopathology, medical management and dental implications," *J. Am. Dent. Assoc.* (2006) 137: 1240-1251.

Grundman et al., "Mild cognitive impairment can be distinguished from Alzheimer Disease and normal aging for clinical trials," *Arch Neurol.* (2004) 61: 59-66.

Leeuwen et al., "Molecular misreading: a new type of transcript mutation expressed during aging," *Neurobiology of Aging* (2000) 21: 879-891.

Lester-Coll et al., "Intracerebral streptozotocin model of type 3 diabetes: Relevance to sporadic Alzheimer's disease," *Journal of Alzheimer's Disease* (2006) 9: 13-33.

Noble et al., "Inhibition of glycogen synthase kinase-3 by lithium correlates with reduced tauopathy and degeneration in vivo," *Proc. Natl. Acad. Sci. USA* (2005) 102 (19): 6990-6995.

Peterson et al., "Neuropathologic Features of Amnestic Mild Cognitive Impairment," *Arch. Neurol.* (2006) 63: 665-672.

Rylett et al., "Acetylcholine synthesis and release following continuous intracerebral administration of NGF in adult and aged Fischer-344 rats," *The Journal of Neuroscience* (1993) 13 (9): 3956-3963.

Sarno et al., "In vivo regulation of GSK3 phosphorylation by cholinergic and NMDA receptors," *Neurobiology of Aging* (2006) 27: 413-422.

Su et al., "Lithium, a common drug for bipolar disorder treatment, regulates amyloid-β precursor protein processing," *Biochemistry* (2004) 43: 6899-6908.

Thorne et al., "Delivery of insulin-like growth factor-I to the rat brain and spinal cord along olfactory and trigeminal pathways following intranasal administration," *Neuroscience* (2004) 481-496.

Xia et al., "Postischemic brain injury is exacerbated in mice lacking the kinin B2 receptor," *Hypertension* (2006) 47: 752-761.

Yan et al., "Matrix metalloproteinase-9 degrades amyloid-β fibrils in Vitro and compact plaques in Situ," *Journal of Biological Chemistry* (2006) 281 (34): 24566-24574.

Yin et al., "Kallikrein/kinin protects against myocardial apoptosis after ischemia/reperfusion via akt-glycogen synthase kinase-3 and Akt-Bad-14-3-3 signaling pathways," *The Journal of Biological Chemistry* (2005) 280 (9): 8022-8030.

Yousef et al., "The new human tissue kallikrein gene family: Structure, function, and association to disease," *Endocrine Reviews* (2001) 22 (2): 184-204.

Zarghooni et al., "Decreased concentration of human kallikrein 6 in brain extracts of Alzheimer's disease patients," *Clin. Biochem.* (2002) 35: 225-231.

Zheng et al., "Amyloid β peptide induces tau phosphorylation and loss of cholinergic neurons in rat primary septal cultures," *Neuroscience* (2002) 115 (1): 201-211.

Aoyagi et al., "Deficiency of kallikrein-like enzyme activities in cerebral tissue of patients with Alzheimer's disease," *Experientia* (1990) 46: 94-97.

Bolan et al., "In vivo micro-MRI of intracortical neurovasculature," *NeuroImage* (2006) 32: 62-69.

Davis et al., "Calibrated functional MRI: Mapping the dynamics of oxidative metabolism," *Proc. Natl. Acad. Sci. USA* (1998) 95: 1834-1839.

Klunk et al., "Imaging brain amyloid in Alzheimer's disease with Pittsburgh Compound-B," *Ann Neurol* (2004) 55: 306-319.

Massa et al., "Alzheimer's therapeutics," *Journal of Molecular Neuroscience* (2002) 19: 107-111.

Supplementary European Search Report for European Application No. EP 08783241.6, mailed Feb. 22, 2012.

International Search Report and Written Opinion for International Application No. PCT/CA2008/001327, mailed Oct. 30, 2008.

Clements, J. et al., "The expanded human kallikrein (KLK) gene family: Genomic organization, tissue-specific expression and potential functions," Biological Chemistry, 382(1):5-14, 2001.

Clements, J. A., "The human kallikrein gene family: a diversity of expression and function," Molecular and Cellular Endocinology, 99:C1-C6, 1994.

Goard, C. et al., "A consolidated catalogue and graphical annotation of dbSNP polymorphisms in the human tissue kallikrein (KLK) locus," Molecular Oncology, 1:303-312, 2007.

Laxmikanthan et al., Proteins: Structure, Function, and Bioinformatics, 58:802-814, 2005.

Montanari et al.; Kallikrein gene delivery improves serum glucose and lipid profiles and cardiac function in streptozotocin-induced diabetic rats; Diabetes, 54:1573-158 0, 2005.

Moreau, M. E. et al., "The kallikrein-kinin system: current and future pharmacological targets," Journal of Pharmacological Sciences, 99:6-38, 2005.

Tschope et al., "Functional, biochemical, and molecular investigations of renal kallikrein-kinin system in diabetic rats," *Am. J. Phisol. Heart Circ. Physiol.*, 277:H2333-H2340, 1999.

Yao, Y. et al., "Tissue kallikrein promotes neovascularization and improves cardic function by the Akt-glycogen synthase kinase-3β pathway," Cardiovascular Research, 80(3):354-364, 2008.

Yousef, G. M. et al., "Role of kallikrein enzymes in the central nervous system," Clinica Chimica Acta, 329(1-2):1-8, 2003.

Zhao et al.; Gene therapy with human tissue kallikrein reduces hypertension and hyperinsulinemia in fructose-induced hypertensive rats; Hypertension, 42:1026-1033, 2003.

* cited by examiner

*** p<0.0001 (1-way ANOVA) ) represents statistically significant difference compared to the vehicle (=10μM Aβ$_{1-42}$) group.

*** p<0.0001 (1-way ANOVA) ) represents statistically significant difference compared to the vehicle (=10μM Aβ$_{1-42}$) group.

*** p<0.0001 (1-way ANOVA) ) represents statistically significant difference compared to the vehicle (=10μM Aβ$_{1-42}$) group.

*** p<0.0001 (1-way ANOVA) ) represents statistically significant difference compared to the vehicle (=10μM Aβ$_{1-42}$) group.

*** p<0.0001 (1-way ANOVA) ) represents statistically significant difference compared to the vehicle (=10μM Aβ$_{1-42}$) group.

*** $p < 0.0001$ (1-way ANOVA) ) represents statistically significant difference compared to the vehicle (=10μM A$\beta_{1-42}$) group.

*** p<0.0001 (1-way ANOVA) ) represents statistically significant difference compared to the vehicle (=10μM Aβ1-42) group.

*** p<0.0001 (1-way ANOVA) ) represents statistically significant difference compared to the vehicle (=10μM Aβ1-42) group.

TISSUE KALLIKREIN FOR THE TREATMENT OF DISEASES ASSOCIATED WITH AMYLOID PROTEIN

CROSS REFERENCE TO RELATED APPLICATIONS

This application is a national stage entry under 35 U.S.C. §371 of PCT/CA2008/001327, filed Jul. 18, 2008, which claims priority from US patent application Ser. No. 60/950,960, filed on Jul. 20, 2007; U.S. patent application Ser. No. 61/023,505, filed on Jan. 25, 2008; U.S. patent application Ser. No. 61/056,411, filed on May 27, 2008; and U.S. patent application Ser. No. 61/061,322, filed on Jun. 13, 2008; the contents of which are hereby incorporated by reference.

FIELD OF THE INVENTION

The present invention relates to methods of treating diseases associated with amyloid protein, including Alzheimer's disease, Alzheimer's precursor amnesic mild cognitive impairment, and associated conditions.

BACKGROUND OF THE INVENTION

Alzheimer's disease is a fatal neurodegenerative disorder currently affecting more than 20 million people worldwide and with increasing rates of occurrence. It is estimated that the incidence rate will double over the next 30 years making Alzheimer's disease a leading cause of mortality among the elderly (van Leeuwen et al., *Neurobiology of Aging*, 2000, 21: 879-891). Characteristics include declination of intellectual functions (memory, language, visiospatial skills and problem solving skills) and decreased abstract reasoning along with abnormal behaviors. Alzheimer's disease results in eventual loss of motor function, inanition and death (Friedlander et al., *Clinical Practice* 2006, 137: 1240-1251). Alzheimer's disease generally occurs later in life and is said to be of "late-onset." The prevalence of Alzheimer's disease in people aged 65-74 years is 3%, while prevalence in age groups 75-84 years and 85 years and older are 19% and 47%, respectively (Friedlander et al., 2006). The average lifespan of an individual diagnosed with Alzheimer's disease is 8-10 years following onset (Friedlander et al., 2006).

As a precursor to being diagnosed with Alzheimer's disease, many first experience amnesic mild cognitive impairment (MCI), which is thought to be a transition stage between normal aging and Alzheimer's disease or a preclinical stage of Alzheimer's disease (*Arch Neurol.* 2004 January; 61(1): 59-66). When memory loss is the predominant feature, this type of impairment is referred to as amnesic MCI and is likely to convert to Alzheimer's disease over time as cognitive decline increases.

Alzheimer's disease is grouped into seven stages, each more debilitating than the last. The first stage is characterized by retrospective analysis once symptoms of Alzheimer's disease have progressed leading to the final stage consisting of dementia and severe cognitive function declination often requiring fulltime home care for the patient (Friedlander et al., 2006) resulting in enormous health care expenditures.

Alzheimer's disease incidence appears to correlate with certain risk factors. These risk factors include head trauma, ethnicity, high-calorie high-fat low-folate diet, limited education, hypercholesterolemia, diabetes mellitus and a sedentary lifestyle. An autosomal dominant inheritance pattern is observed in about 5% of cases which display familial incidence (Friedlander et al., 2006).

The exact cause of Alzheimer's disease is not currently known, however, the disease is regulated by many pathways in an extremely complicated fashion. Pathways include defective metabolism of beta-amyloid protein (A$\beta$), abnormal neurotransmission (glutamine, andrenergic, serotonin and dopamine), inflammation, hormonal and oxidative pathways (Frank et al., *Ann. Clin. Psychiatry* 2005, 17(4): 269-286). Four genes appear to be involved in Alzheimer's disease. These genes encode the amyloid precursor protein (APP), presenilin 1, presenilin 2 and apolipoprotein E (Frank et al., 2005). Alzheimer's disease can be characterized in regions of the brain due to the presence of fibrillary plaques or tangles. Plaques are extracellular deposits and tangles observed intracellularly. Plaques contain A$\beta$ and its fragments A$\beta$40 and A$\beta$42 while tangles contain the microtubule-associated protein known as tau (Frank et al., 2005). The A$\beta$ fragments are the products of an abnormal proteolytic cleavage event involving APP (the precursor). Plaques may form in areas of the brain involved in memory formation and information acquisition. N-methyl-D-aspartate (NMDA) receptors are believed to be involved with the neurotoxic events of Alzheimer's disease and A$\beta$ may be directly involved. Tangles are created when tau protein aggregate together after being hyperphosphorylated at specific sites by proteins kinases. In particular, the protein kinase glycogen synthase kinase-3 beta (GSK-3$\beta$) has been implicated in the hypersphorylation of tau (*Proc Natl Acad Sci USA.* 2005 May 10; 102(19):6990-5), leading to tangle formation and axonal microtubule break down. A$\beta$ has been shown to stimulate GSK-3$\beta$ activity within neurons (*Neuroscience* 2002; 115(1): 201-11). The break down of microtubules prevents axonal transport, leads to the loss of synapses, and neurodegeneration.

Common methods of treatment regarding cognitive and functional decline include cholinesterase inhibitors and N-methyl-D-aspartate receptor antagonists. Events of psychoses and agitation may be treated with atypical antipsychotics (such as Olanzapine and Risperidone) and mood stabilizers. Finally, depression and anxiety may be treated with selective serotonin reuptake inhibitors, tricyclic antidepressants, norepinephrine reuptake inhibitors and central $\alpha_2$-adrenergic autoreceptor and heterorecptor antagonists (Friedlander et al., 2006).

In the general population, Alzheimer's disease strikes the majority of patients at a relatively late age, but for those with Down syndrome (also known as "trisomy 21" or "DS"), the disease is more rapid. Most people with Down syndrome develop Alzheimer's pathology by late middle age, including deposits of the plaque-forming protein A$\beta$ that are often more severe than in most other Alzheimer's patients.

SUMMARY OF THE INVENTION

The present invention provides the use of tissue kallikrein or a variant or active fragment thereof in the treatment of Alzheimer's disease or symptoms thereof and in the treatment of amnesic mild cognitive impairment or symptoms thereof. The present invention further provides the use of tissue kallikrein or a variant or active fragment thereof for the digesting or cleaving amyloid and the treatment of conditions benefiting from the digestion or cleavage of amyloid.

In one aspect, provided is a method of treating a patient having: (a) Alzheimer's disease or symptoms thereof; or (b) amnesic mild cognitive impairment or symptoms thereof, said method comprising administering a therapeutically effective amount of tissue kallikrein or a variant or active fragment thereof to said patient.

In an embodiment of the invention, the tissue kallikrein, or a variant or active fragment thereof, is administered concurrently with a second therapeutic compound useful in treating Alzheimer's disease or amnesic mild cognitive impairment.

In another aspect, provided is a pharmaceutical composition comprising about 1 to about 1000 IU per day of tissue kallikrein, or a variant or active fragment thereof, and a pharmaceutically acceptable excipient formulated for oral administration.

In another aspect, provided is a pharmaceutical composition comprising about 0.001 to about 5000 IU per dosage frequency, or a variant or active fragment thereof, and a pharmaceutically acceptable excipient formulated for intranasal administration.

In an embodiment, the pharmaceutical composition according to the invention, comprise a tissue kallikrein, or a variant or active fragment thereof combined with an adjuvant.

In a further embodiment of the invention, the adjuvant is an emulsifier.

In a further embodiment, the pharmaceutical composition according to the invention comprises a tissue kallikrein, or a variant or active fragment thereof combined with lipophilic micelles.

In a further embodiment, the pharmaceutical composition according to the invention further comprises a second therapeutic compound useful in treating Alzheimer's disease.

In another aspect, provided is the use of a tissue kallikrein, or a variant or active fragment thereof for the preparation of a medicament useful for treating: (a) Alzheimer's disease or symptoms thereof, or (b) amnesic mild cognitive impairment or symptoms thereof.

In another aspect, provided is the use of a therapeutically effective amount of tissue kallikrein, or a variant or active fragment thereof for the treatment of: (a) Alzheimer's disease or symptoms thereof, or (b) amnesic mild cognitive impairment or symptoms thereof.

In an embodiment of the invention, the tissue kallikrein, or a variant or active fragment thereof, use further comprises the concurrent use of a second therapeutic compound useful in treating Alzheimer's disease or amnesic mild cognitive impairment.

In further embodiments of the invention, the second therapeutic compound comprises an acetylcholine precursor, a compound that enhances acetylcholine release, an acetylcholinesterase inhibitor, a muscarinic agonist, an antioxidant, an anti-inflammatory agent, a hormone, a calcium channel blocker, nerve growth factor, a nootropic agent, a neurotrophin small molecule mimetic, NMDA receptor antagonists, a 5-HT1A receptor agonist, an antiamyloidogenic agent, an antihistimine, an ergoloid mesylate, ginko biloba, or huperazine A.

In further embodiments of the invention, the acetylcholinesterase precursor is selected from choline, lecithin, or acetyl-1-carnitine.

In further embodiments of the invention, the compound that enhances acetylcholine release is 4-aminopyridine or linopirdine.

In further embodiments of the invention, the acetylcholinesterase inhibitor is selected from physostigmine, tacrine, donepezil, rivastigmine, galanthamine, metrifonate, huperazine A, or eptastigmine.

In further embodiments of the invention, the muscarinic agonist is selected from milameline, xanomeline, arecoline, oxotremorine, sabcomeline, or talsaclidine.

In further embodiments of the invention, the antioxidant is selected from vitamin E, idebenone, co-enzyme Q-10, n-acetyl cysteine, or vitamin C.

In further embodiments of the invention, the anti-inflammatory agent is a non-steroidal ant-inflammatory agent.

In further embodiments of the invention, the hormone is estrogen or testosterone.

In further embodiments of the invention, the nootropic agents is piracetam.

In further embodiments of the invention, the ergoloid mesylate is hydergine.

In further embodiments of the invention, the therapeutically effective amount of tissue kallikrein, or a variant or active fragment thereof is administered intranasally.

In further embodiments of the invention, the therapeutically effective dose is about 0.001 to about 5000 International Units (IU) dosage frequency.

In further embodiments of the invention, the therapeutically effective amount of tissue kallikrein, or a variant or active fragment thereof is administered orally.

In further embodiments of the invention, the therapeutically effective of tissue kallikrein, or a variant or active fragment thereof is about 0.001 to about 1000 IU per day.

In a further aspect, provides is the use of a therapeutically effective amount of tissue kallikrein, or a variant or active fragment thereof for digesting or cleaving amyloid in a patient in need thereof.

In a further aspect, provides is the use of a therapeutically effective amount of tissue kallikrein, or a variant or active fragment thereof for improving neurovasculature of a patient in need thereof.

In a further aspect, provides is the use of a therapeutically effective amount of tissue kallikrein, or a variant or active fragment thereof for improving oxygen uptake to the brain of a patient in need thereof.

In a further aspect, provides is the use of a therapeutically effective amount of tissue kallikrein, or a variant or active fragment thereof for improving blood flow to the brain of a patient in need thereof.

In a further aspect, provides is the use of a therapeutically effective amount of tissue kallikrein, or a variant or active fragment thereof for improving plaque clearance in the brain of a patient in need thereof.

In a further aspect, provides is the use of a therapeutically effective amount of tissue kallikrein, or a variant or active fragment thereof for improving glucose uptake by the brain of a patient in need thereof.

In a further aspect, provides is the use of a therapeutically effective amount of tissue kallikrein, or a variant or active fragment thereof for reducing tau phosphorylation in the brain of a patient in need thereof.

DETAILED DESCRIPTION

Definitions

Figure 1:
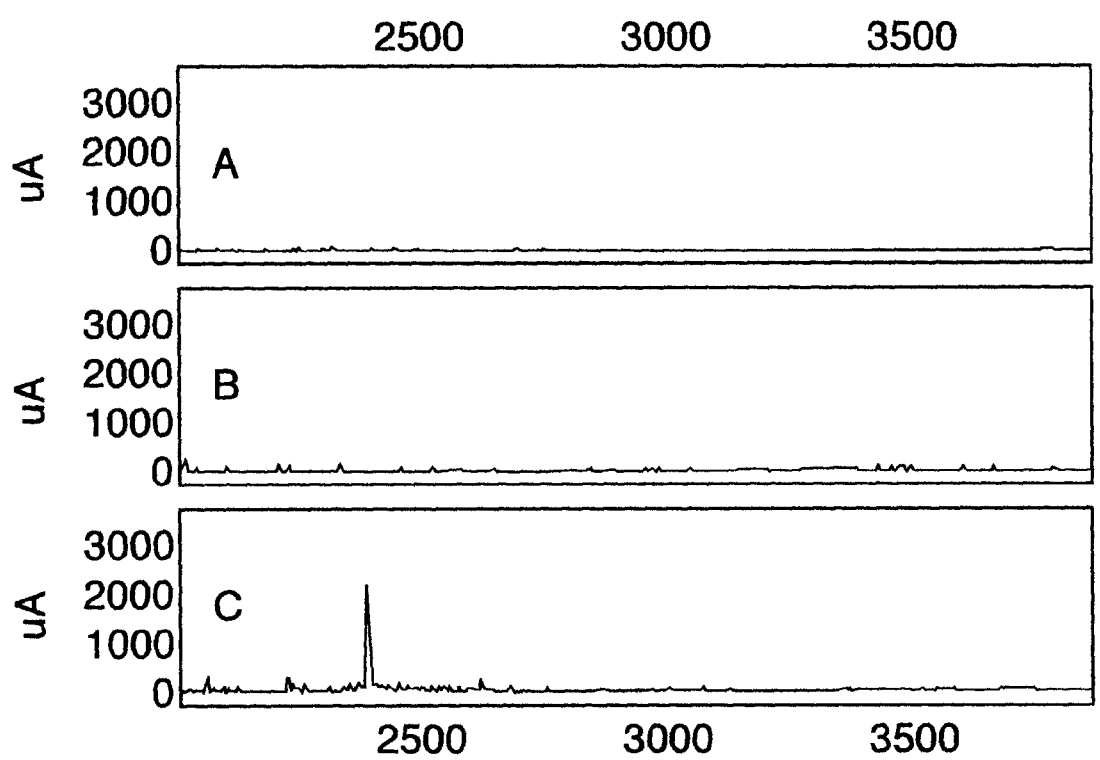
FIG. 1 is mass spectra showing tissue kallikrein (KLK1) cleavage of amyloid fibrils in vitro. A) β-amyloid (Aβ) alone; B) KLK1 alone; and C) KLK1 and Aβ.

"Tissue kallikrein" or "KLK1" is a serine protease that is primarily noted for its role in controlling hypertension through its cleavage of kininogen into lysyl-bradykinin (kallidin) (Yousef et al., *Endocrine Rev.* 2001; 22: 184-204). As there are a large number of enzymes in the KLK family, the inventors believe that KLK1 appears to be a ubiquitous or multiple target acting enzyme, in addition to its recognized role in hypertension regulation and as such may specifically play an important role in treating Alzheimer's disease. As used herein, the term "tissue kallikrein" is synonymous with the following terms: callicrein, glumorin, padreatin, padutin, kallidinogenase, bradykininogenase, pancreatic kallikrein, onokrein P, dilminal D, depot-Padutin, urokallikrein, or urinary kallikrein.

As described above, "kallidin" refers to lysyl-bradykinin. Kallikrein cleaves kininogen into kallidin. Kallidin can activate the bradykinin 2 receptor, which is known to increase the expression of matrix metalloproteinase-9 (MMP-9). MMP-9 can also cleave amyloid.

Tissue kallikrein polypeptide has the following sequence (SEQ ID NO:1):

```
NP_001001911 GI: 50054435 Sus scrofa 1-17 signal peptide 18-24 propeptide 25-263 mature peptide >gi|50054435|ref|NP_001001911.1| kallikrein 1
[Sus scrofa]
MWSLVMRLALSLAGTGAAPPIQSRIIGGRECEKDSHPWQVAIYHYSSFQC
GGVLVDPKWVLTAAHCKNDN

YQVWLGRHNLFENEVTAQFFGVTADFPHPGFNLSLLKNHTKADGKDYSHD
LMLLRLQSPAKITDAVKVLE

LPTQEPELGSTCQASGWGSIEPGPDDFEFPDEIQCVELTLLQNTFCADAH
PDKVTESMLCAGYLPGGKDT

CMGDSGGPLICNGMWQGITSWGHTPCGSANKPSIYTKLIFYLDWINDTIT
ENP
```

Another embodiment includes:

```
NP_002248 GI: 4504875 Homo sapiens 1-18 signal peptide 19-24 propeptide 25-262 mature peptide >gi|4504875|ref|NP_002248.1| kallikrein 1
preproprotein [Homo sapiens]
                                       (SEQ ID NO: 2)
MWFLVLCLALSLGGTGAAPPIQSRIVGGWECEQHSQPWQAALYHFSTFQC
GGILVHRQWVLTAAHCISDN

YQLWLGRHNLFDDENTAQFVHVSESFPHPGFNMSLLENHTRQADEDYSHD
LMLLRLTEPADTITDAVKVV

ELPTEEPEVGSTCLASGWGSIEPENFSFPDDLQCVDLKILPNDECKKAHV
QKVTDFMLCVGHLEGGKDTC

VGDSGGPLMCDGVLQGVTSWGYVPCGTPNKPSVAVRVLSYVKWIEDTIAE
NS
```

The term "active fragment" refers to smaller portions of the KLK1 polypeptide that retains the activity of the full-length KLK1 polypeptide.

A "variant" or "mutant" of a starting or reference polypeptide is a polypeptide that 1) has an amino acid sequence different from that of the starting or reference polypeptide and 2) was derived from the starting or reference polypeptide through either natural or artificial (man made) mutagenesis. Such variants include, for example, deletions from, and/or insertions into and/or substitutions of, residues within the amino acid sequence of the polypeptide of interest. A variant amino acid, in this context, refers to an amino acid different from the amino acid at the corresponding position in a starting or reference polypeptide sequence (such as that of a source antibody or antigen binding fragment). Any combination of deletion, insertion, and substitution may be made to arrive at the final variant or mutant construct, provided that the final construct possesses the desired functional characteristics. The amino acid changes also may alter post-translational processes of the polypeptide, such as changing the number or position of glycosylation sites. Methods for generating amino acid sequence variants of polypeptides are described in U.S. Pat. No. 5,534,615, expressly incorporated herein by reference.

A "wild type" or "reference" sequence or the sequence of a "wild type" or "reference" protein/polypeptide maybe the reference sequence from which variant polypeptides are derived through the introduction of mutations. In general, the "wild type" sequence for a given protein is the sequence that is most common in nature. Similarly, a "wild type" gene sequence is the sequence for that gene which is most commonly found in nature. Mutations may be introduced into a "wild type" gene (and thus the protein it encodes) either through natural processes or through man induced means. The products of such processes are "variant" or "mutant" forms of the original "wild type" protein or gene.

"Percent (%) amino acid sequence identity" with respect to the polypeptides identified herein is defined as the percentage of amino acid residues in a candidate sequence that are identical with the amino acid residues in the reference sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MegAlign (DNASTAR) software. Those skilled in the art can determine appropriate parameters for measuring alignment, including any algorithms needed to achieve maximal alignment over the full length of the sequences being compared. The ALIGN-2 program is publicly available through Genentech, Inc., South San Francisco, Calif.

For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y,$$

where X is the number of amino acid residues scored as identical matches by the sequence alignment program in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

"Percent (%) nucleic acid sequence identity" is defined as the percentage of nucleotides in a candidate sequence that are identical with the nucleotides in a reference polypeptide-encoding nucleic acid sequence, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN, ALIGN-2 or MegAlign (DNASTAR) software. Appropriate parameters for measuring alignment, including any algorithms needed to achieve maximal alignment over the full-length of the sequences being compared can be determined by known methods.

For purposes herein, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z, where W is the number of nucleotides scored as identical matches by the sequence alignment program in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C.

The term "amino acid" is used in its broadest sense and is meant to include the naturally occurring L α-amino acids or residues. The commonly used one and three letter abbreviations for naturally occurring amino acids are used herein (Lehninger, A. L., Biochemistry, 2d ed., pp. 71-92, (1975), Worth Publishers, New York). The term includes all D-amino acids as well as chemically modified amino acids such as amino acid analogs, naturally occurring amino acids that are not usually incorporated into proteins such as Norleucine, and chemically synthesized compounds having properties known in the art to be characteristic of an amino acid. For example, analogs or mimetics of phenylalanine or proline, which allow the same conformational restriction of the peptide compounds as natural Phe or Pro are included within the definition of amino acid. Such analogs and mimetics are referred to herein as "functional equivalents" of an amino acid. Other examples of amino acids are listed by Roberts and Vellaccio, In: The Peptides: Analysis, Synthesis, Biology, Gross and Meiehofer, Eds., Vol. 5 p 341, Academic Press, Inc, N.Y. 1983, which is incorporated herein by reference.

The term "protein" has an amino acid sequence that is longer than a peptide. A "peptide" contains 2 to about 50 amino acid residues. The term "polypeptide" includes proteins and peptides. Examples of proteins include, but are not limited to, antibodies, enzymes, lectins and receptors; lipoproteins and lipopolypeptides; and glycoproteins and glycopolypeptides.

A "fusion protein" and a "fusion polypeptide" refer to a polypeptide having two portions covalently linked together, where each of the portions is a polypeptide having a different property. The property may be a biological property, such as activity in vitro or in vivo. The property may also be a simple chemical or physical property, such as binding to a target antigen, catalysis of a reaction, etc. The two portions may be linked directly by a single peptide bond or through a peptide linker containing one or more amino acid residues. Generally, the two portions and the linker will be in reading frame with each other. Preferably, the two portions of the polypeptide are obtained from heterologous or different polypeptides.

The term "therapeutically effective amount" refers to an amount of a composition of this invention effective to "alleviate" or "treat" a disease or disorder in a subject or mammal. Generally, alleviation or treatment of a disease or disorder involves the lessening of one or more symptoms or medical problems associated with the disease or disorder. In some embodiments, it is an amount that improves neurovasculature, oxygen uptake, blood flow, plaque clearance, glucose uptake, cleavage of fibrils, breakdown of plaques, plaque burden, reduction of tau phorphorylation and mixtures thereof.

The terms "treatment" and "treating" refer to inhibiting, alleviating, and healing amyloid protein associated diseases, including, but not limited to Alzheimer's disease, amnesiac MCI, and conditions or symptoms thereof. "Treating" or "treatment" refers to both therapeutic treatment and prophylactic or preventative measures, wherein the object is to prevent or slow down (lessen) the targeted pathologic condition or disorder. Treatment can be carried out by administering a therapeutically effective amount of at least one compound of the invention. A "therapeutically effective amount" as used herein includes a prophylactic amount, for example an amount effective for alleviating or healing the above mentioned diseases or symptoms thereof. These parameters for assessing successful treatment and improvement in the disease are readily measurable by routine procedures familiar to a physician.

The term "improved neurovasculature" refers to the increase of blood vessel density or increased nutrient delivery to the brain through the blood vessel network. The use of high resolution magnetic resonance imaging (MRI), known to one skilled in the art allows for the development of a three dimensional (3D) vascular network map of the imaged brain. The use of endogenous blood oxygenation level-dependent contrast and exogenous contrast agent allows for the visualization of artery and vein structures within the 3D image (Bolan et. al, 2006). Comparison of the vascular network before treatment, during treatment and after treatment allows for assessment of improved neurovasculature for a particular Alzheimer's disease patient undergoing treatment. An "increase" refers to a greater blood vessel density or greater nutrient delivery to the brain in a patient after treatment compared to the blood vessel density or nutrient delivery in the patient before treatment.

The term "improved oxygen uptake" refers to the increased delivery of oxygen to the brain and cells of the brain while the term "improved blood flow" refers to an increase of blood volume circulating through the brain. The use of functional MRI, as well established in the art, allows for the visualization of blood flow in the brain (Davis et. al, 1998). An area of the brain that undergoes activity requires oxygen to aid in the metabolism of glucose for energy. This is achieved by a large increase in blood flow so that the diffusion limitation of oxygen is overcome and is supplied in plentiful amounts to the active brain tissue. This increase in blood flow and accompanying increase in oxygen is detected through changes in the endogenous blood oxygenation level-dependent contrast by functional MRI. The increased signal is then used to derive the increase in blood flow and oxygen uptake and metabolism. By mapping the areas of blood flow and oxygen uptake deficiencies in the brain of an Alzheimer's disease patient, improvement can be assessed during and after treatment using age matched non-Alzheimer's disease patient as a control. An "increase" refers to greater oxygen uptake or blood flow in a patient after treatment compared to the oxygen uptake or blood flow in the patient before treatment.

The term "improved plaque clearance" refers to a measurable decrease in plaque area. Positron emission tomography (PET) and the use of a contrasting agent with specificity toward plaque (e.g. thioflavin derivative Pittsburgh Compound-B, PIB) (Klunk et al, 2004), is a method known in the art to visualize plaque deposition in the brain of an Alzheimer's disease patient. By generating images of plaque burden one can assess the improvement in clearance of plaque as a result of treatment in comparison to before treatment and age-matched non-Alzheimer's disease control subjects.

The term "improved glucose uptake" refers to the enhanced ability of the brain to utilize glucose from the blood stream. One of the hallmarks of Alzheimer's disease is the reduction of glucose uptake and metabolism by cells of the brain (hypometabolism); this marker of disease onset is determined by the use of PET imaging of the brain with fluorine labeled glucose contrast agent (FDG-PET) (Buckner et. al, 2005). By comparing images generated by this method before, during and after treatment, an improvement in glucose uptake in areas of the brain in an Alzheimer's disease patient previously displaying a reduction of glucose uptake can be assessed while using age-matched non-Alzheimer's disease control subjects.

The term "improved cleavage of fibrils" refers to the enhanced ability to proteolytically digest fibrils.

The term "breakdown of plaque" refers to the outcome of the proteolytic cleavage of fibrils.

The term "plaque burden" refers to the total amount of aggregated fibrils which make up plaque.

The term "reduction of tau phosphorylation" refers to a decreased amount of tau protein phosphorylation within cells of the brain.

Methods of Treating Alzheimer's Disease and Amnesiac Mild Cognitive Impairment

The present invention provides the use of a therapeutically effective amount tissue kallikrein or a variant or active fragment thereof in the treatment of Alzheimer's disease or symptoms thereof. In an embodiment of the invention, the tissue kallikrein, or a variant or active fragment thereof, may be administered concurrently with a second therapeutic compound useful in treating Alzheimer's disease. Examples of compounds useful in the treatment of Alzheimer's disease are discussed in greater detail below. The therapeutically effective amount tissue kallikrein or a variant or active fragment thereof may be administered orally or more preferably, intranasally. Methods of administration of discussed in greater detail below.

The present invention further provides the use of tissue kallikrein or a variant or active fragment thereof in the treatment of conditions associated with Alzheimer's disease including neurological conditions such as memory, language, visiospatial skills and problem solving and psychological conditions such as apathy, irritability, anxiety, depression, delusions, hallucinations, insomnia, anorexia, psychosis inanition, incontinence, or social withdrawal.

Alzheimer's disease is associated with brain-specific abnormalities in insulin and signaling mechanisms (Lester-Coll et al., *J. Alzheimers Dis.* 2006, 9(1):13-33 (Abstract only)). Animal models show neurodegeneration due to increased levels of phosphorylated tau protein and Aβ and upregulated expression of the genes encoding tau protein and amyloid precursor protein. These alterations in gene expression directly result in decreased expression of genes encoding insulin, insulin-like growth factor II and a variety of insulin related receptors (insulin receptor, insulin-like growth factor I receptor, insulin receptor substrate-I, insulin-like growth factor II receptors) and reduced ligand binding to the insulin receptor. (Lester-Coll et al., 2006). Patients with Alzheimer's disease often have reduced glucose uptake and metabolism in brain cells due to insulin abnormalities Another embodiment of the invention includes the use of a therapeutically effective amount tissue kallikrein or a variant or active fragment thereof for improving glucose uptake by the brain of a patient.

Amyloid plaque deposition is the major pathology associated with Alzheimer's disease. It has been shown that plaque clearance is possible with endogenous proteinases such as Matrix Metalloproteinase 9 (MMP-9) (Yan, 2006)

As KLK1 has the ability to protect against amyloid challenge, KLK1 can also be of benefit to treating Down syndrome patients. Down syndrome is caused by an extra copy of chromosome 21, which can lead to the overexpression of certain proteins. The amyloid precursor protein (APP), which is cleaved to form Aβ, is located on chromosome 21, and presumably its increased production contributes to the early onset of Alzheimer's disease in Down syndrome patients.

KLK1 can directly cleave fibrillary amyloid plaques. The ability to cleave these hallmarks of disease associated with amyloid protein could reduce plaques in Alzheimer's disease, and Down syndrome. Direct cleavage of these fibrillary amyloid plaques can treat these diseases, for example help Alzheimer's disease associated cognitive decline.

Another embodiment of the invention is the use of a therapeutically effective amount of tissue kallikrein, or a variant or active fragment thereof for digesting or cleaving amyloid. Another embodiment of the invention is the use of a therapeutically effective amount of tissue kallikrein, or a variant or active fragment thereof for improving plaque clearance in the brain of a patient in need thereof. Tissue kallikrein, or a variant or active fragment thereof can be used for improved cleavage of fibrils. The proteolytic cleavage of fibrils results in the reduction in the total amount of aggregated fibrils which make up fibrillary amyloid plaques and consequently results in improved plaque clearance from the brains of affected patients.

Activity of GSK-3β kinase is an essential factor in the progression of Alzheimer's disease through its phosphorylation of tau and APP. Formation of tangles resulting from phosphorylation of tau leads to neurodegeneration, while the processing of APP into Aβ is favoured when phosphorylated leading to amyloid plaque formation. Direct inhibition of GSK-3β with specific inhibitors such as lithium reduces tau phosphorylation, tangles, neurodegeneration, and APP processing into Aβ (*Biochemistry* 2004 Jun. 8; 43(22):6899-908; *Proc Natl Acad Sci USA.* 2005 May 10; 102(19):6990-5). Another embodiment of the invention is the use of a therapeutically effective amount of tissue kallikrein, or a variant or active fragment thereof for reducing tau phosphorylation in the brain of a patient in need thereof.

Activity of GSK-3β is normally regulated by serine 9 phosphorylation by Akt. Interestingly, activation of the bradykinin B2 receptor signaling pathway by kinin (*J Biol Chem.* 2005 Mar. 4; 280(9):8022-30) and the NGF-acetylcholine pathway leads to increased GSK-3β phosphorylation (*J Neurosci.* 1993 September; 13(9):3956-63; *Neurobiol Aging* 2006 March; 27(3):413-22). Both pathways are thought to be mediated by extracellular proteases, including KLK1 (*FEBS Lett.* 1990 Jul. 16; 267(2):207-12; *Hypertension* 2006 April; 47(4):752-61).

Another embodiment of the invention is the use of a therapeutically effective amount of tissue kallikrein, or a variant or active fragment thereof for reducing tau phosphorylation in the brain of a patient in need thereof.

Neurovascular dysfunction is known to contribute to the pathology and progression of Alzheimer's disease. Neurovascular dysfunction may result from inflammation caused by poor plaque clearance.

Another embodiment of the invention is the use of a therapeutically effective amount of tissue kallikrein, or a variant or active fragment thereof for improving neurovasculature of a patient in need thereof. In a further embodiment, the use includes the improvement blood flow and/or the improvement of oxygen uptake to the brain of a patient in need thereof.

Amnesiac MCI represents an intermediate state between normal cognition and dementia seen in Alzheimer's disease. Therefore, not surprisingly, neuropathological expression of amnesic MCI presents itself as a transition state towards Alzheimer's disease. In particular, predominant expression of tau tangles within the medial temporal lobe structures of the brain and an amyloid burden more similar to that found in normal healthy individuals (*Arch Neurol.* 2006 May; 63(5): 665-72) is found in amnesic MCI. As such, underlying mechanisms involved in the pathology described for Alzheimer's disease are at play in amnesic MCI and therefore the same therapeutic actions of KLK1 used to treat Alzheimer's disease are applicable in treating amnesic MCI and progression towards Alzheimer's disease.

As such, a method of treating Alzheimer's disease or amnesic MCI through the administration of KLK1, variant or active fragment thereof improves plaque clearance in the brain.

Another aspect of the invention includes the use of use of a therapeutically effective amount tissue kallikrein or a variant or active fragment thereof for the treatment of amnesic MCI. One embodiment includes a method of treating amnesiac MCI in a mammal by orally, or more preferably, intranasally administering a therapeutically effective amount of tissue kallikrein.

In a further embodiment, the tissue kallikrein can be administered concurrently with a second therapeutic compound useful for treating Alzheimer's disease or amnesiac MCI. Examples of such compounds are described in greater detail below.

Administration of Tissue Kallikrein

Traditional modes of drug administration to treat aliments in the brain include oral as well as intravenous routes of administration. These modes are not always ideal. Oral administration of compounds results in limited bioavailability (solubility, $1^{st}$ pass liver degredation, blood brain barrier restriction) as well as time release issues with potentially undesirable gastrointestinal side effects. However, tissue tissue kallikrein (KLK1) appears able to pass through and may bypass the blood-brain-barrier to produce its effects on the brain.

Intravenous (i.v.) administration requires trained medical professionals, which is time consuming and costly to the health care system. It may also result in patient compliance issues. Risks associated with intravenous administration, include infection at the injection site and safety issues to both the patient and the professional administering the dose. However, in a controlled setting, intravenous administration can be effective.

Intranasal administration allows a medicament to be 'fast acting' since it is able to reach the brain by a more direct route. Intranasal administration is convenient and virtually eliminates issues of patient compliance as seen with intravenous administration. Olfactory epithelial cells are selectively permeable. Thus, proteins such as KLK1 can pass through and may bypass the blood-brain-barrier via the intranasal route. Thereby intranasal administration of KLK1 may produce its effects directly on the brain—thereby minimizing peripheral effects as well. This is due to involvement of the olfactory region in the upper portion of the nasal pathway.

There are two possible routes that a substance administered intranasally may follow at the olfactory region—intraneuronal and extraneuronal. An intraneuronal route includes uptake of peptides into olfactory neurons where peptides travel along axons to bypass the blood-brain-barrier. Passage through unique intercellular clefts in epithelia of the olfactory region is an extracellular route that allows peptides to diffuse into the subarachnoid space. An extracellular route is more preferable due to rapid passage time to the brain, avoidance of proteolytic degradation involved in intraneuronal pathways (Born et al., *Nat. Neurosci.* 2002, 5(6):514-6), and rapid eliciting of biological effects at multiple sites of the brain (Throne et al., 2004).

Intranasal administration can provide an advantage over oral administration by more direct delivering KLK1 to desired sites of action (the brain).

Pharmaceutical compositions may be administered orally or intranasally. Formulations suitable for intranasal administration include ointments, creams, lotions, pastes, gels, sprays, aerosols, oils and the like. Solutions or suspensions are applied directly to the nasal cavity by conventional means, for example, with a dropper, pipette or spray. Formulations may be provided in a single or multidose form. In the latter case of a dropper or pipette, this may be achieved by the patient administering an appropriate, predetermined volume of the solution or suspension. A spray includes a metering atomizing spray pump.

Formulations for aerosol administration, particularly to the upper respiratory tract containing the nasal cavity and olfactory region, include intranasal administration. An active ingredient is provided in a pressurized pack with a suitable propellant including, but not limited to, a chlorofluorocarbon (CFC), dichlorodifluoromethane, trichlorofluoromethane, or dichlorotetrafluoroethane, or carbon dioxide or other suitable gas. An aerosol may also contain a surfactant such as lecithin. A dose of drug may be controlled by a metered valve. Alternatively active ingredients may be provided in a form of a dry powder. A powder mix of the compound can be in a suitable powder base such as lactose, starch, or starch derivatives such as hydroxypropylmethyl cellulose and polyvinylpyrrolidine (PVP). The powder carrier can form a gel in the nasal cavity. A powder composition may be presented in unit dose form, including, but not limited to, capsules or cartridges (e.g., gelatine or blister packs from which the powder may be administered by means of an inhaler).

Oral administration includes enteral administration of solution, tablets, sustained release capsules, enteric coated capsules, orally disintegrating tablets and syrups.

An "effective amount" or a "therapeutically effective amount" refers to a nontoxic but sufficient amount of drug or agent to provide a desired effect. In a combination therapy, an "effective amount" of one component of the combination is an amount of that compound that is effective to provide a desired effect when used in combination with the other components of the combination. An amount that is "effective" will vary from subject to subject, depending on the age and general condition of an individual, a particular active agent or agents, and the like. An appropriate "effective" amount in any individual case may be determined using routine experimentation.

A therapeutically effective amount of a compound of the invention for treating the above-identified diseases or symptoms thereof can be administered prior to, concurrently with, or after the onset of the disease or symptom. A compound of the invention can be administered concurrently with the onset of the disease or symptom. "Concurrent administration" and "concurrently administering" as used herein includes administering a polypeptide of the invention and another therapeutic agent in admixture, such as, for example, in a pharmaceutical composition or in solution, or separately, such as, for example, separate pharmaceutical compositions or solutions administered consecutively, simultaneously, or at different times, but not so distant in time such that the compound of the invention and the other therapeutic agent cannot interact and a lower dosage amount of the active ingredient cannot be administered.

Another aspect of the present invention includes a method as described herein further comprising concurrently administering an additional therapeutic compound useful in treating Alzheimer's disease. An Alzheimer's disease therapeutic compound includes, but is not limited to, an acetylcholine precursor, a compound that enhances acetylcholine release, an acetylcholinesterase inhibitor, a muscarinic agonist, an antioxidant, an anti-inflammatory agent, a hormone, a calcium channel blocker, nerve growth factor, a nootropic agent, a neurotrophin small molecule mimetic (Massa et al., *J. Mol. Neurosci.* 2002, 19: 107-111), NMDA receptor antagonists, a 5-HT1A receptor agonist such as xaliproden, an antiamyloidogenic agent such as tramiprosate (Alzemed™), an antihistimine such as Dimebon™, an ergoloid mesylate (HYDERGINE®), ginko biloba, and huperazine A. Such compounds may also be useful for treating amnesiac MCI.

A further aspect of the invention includes an acetylcholine precursor that can be choline, lecithin, or acetyl-1-carnitine.

A compound that enhances acetylcholine release includes, but is not limited to, 4-aminopyridine or linopirdine.

An acetylcholinesterase (AChE) inhibitor includes, but is not limited to, physostigmine, tacrine, donepezil, rivastigmine, galantamine (RAZADYNE®), metrifonate, huperazine A, or eptastigmine.

A muscarinic agonist includes, but is not limited to, milameline, xanomeline, arecoline, oxotremorine, sabcomeline, or talsaclidine.

An antioxidant includes, but is not limited to, vitamin E, idebenone, co-enzyme Q-10, n-acetyl cysteine, or vitamin C.

An anti-inflammatory agent includes non-steroidal anti-inflammatory agents.

A hormone includes, but is not limited to, estrogen or testosterone.

A nootropic agent includes, but is not limited to, piracetam, aniracetam, fosracetam, nefiracetan, pramiracetam, nebracetam, and oxiracetam.

An NMDA receptor antagonist includes, but is not limited to, memantine; ketamine; MK-801; L-701,324; L-689,560; GV196771A; 2-amino-5-phosphonopentanoic acid (AP5); (R)-CPP-ene; and (2S*,3R*)-1-(biphenyl-4-carbonyl)piperazine-2,3-dicarboxylic acid (PBPD).

"Treatment" and "treating" refer to preventing, inhibiting, and/or alleviating a disease and related symptoms as well as healing disease conditions or symptoms affecting mammalian organs and tissues. A composition of the present invention can be administered in a therapeutically effective amount to a patient before, during, and after any mentioned condition arises.

Pharmaceutical Compositions

The present invention provides pharmaceutical compositions comprising tissue kallikrein, or a variant or active fragment thereof suitable for oral and intranasal administration in the treatment of Alzheimer's disease, amnesiac MCI and symptoms thereof.

In one aspect, the present invention provides a pharmaceutical composition comprising about 0.001 to about 1000 International Units (IU) per dosage frequency of tissue kallikrein, or a variant or active fragment thereof, and a pharmaceutically acceptable excipient formulated for oral administration. An intranasal dose of tissue kallikrein, or a variant or active fragment thereof can be about 0.001 to 100 IU. An intranasal dose of tissue kallikrein, or a variant or active fragment thereof can be about 0.001 to 10 IU. An intranasal dose of tissue kallikrein, or a variant or active fragment thereof can be about 0.01 to 10 IU. An intranasal dose of tissue kallikrein, or a variant or active fragment thereof can be about 0.01 to 1 IU. An intranasal dose of tissue kallikrein, or a variant or active fragment thereof can be about 0.1 to 1 IU.

In another aspect, the present invention provides a pharmaceutical composition comprising about 0.001 to about 5000 IU per dosage frequency of tissue kallikrein, or a variant or active fragment thereof, and a pharmaceutically acceptable excipient formulated for intranasal administration. An oral dose of tissue kallikrein, or a variant or active fragment thereof can be about 0.001 to 500 IU. An oral dose of tissue kallikrein, or a variant or active fragment thereof can be about 0.001 to 50 IU. An oral dose of tissue kallikrein, or a variant or active fragment thereof can be about 0.01 to 50 IU. An oral dose of tissue kallikrein, or a variant or active fragment thereof can be about 0.01 to 5 IU. An oral dose of tissue kallikrein, or a variant or active fragment thereof can be about 0.1 to 5 IU. An oral dose of tissue kallikrein, or a variant or active fragment thereof can be about 0.1 to 1 IU.

The pharmaceutical composition may further comprise a second therapeutic compound useful in treating Alzheimer's disease or amnesiac MCI as discussed above.

Pharmaceutical compositions of the invention include formulations to be administered orally or intranasally. Formulations suitable for intranasal administration include powder, granules, solution, drops, ointments, creams, lotions, pastes, gels, sprays, aerosols, oils and the like. Solutions or suspensions of the invention can be applied directly to the nasal cavity by conventional means, for example, with a dropper, pipette or spray. Formulations may be provided in a single or multidose form. A solution may be sterile, isotonic or hypotonic, and otherwise suitable for administration by injection or other means and may contain appropriate adjuvants, buffers, preservatives and salts. Solutions such as nose drops may contain antioxidants, buffers, and the like. Powder or granular forms of a pharmaceutical composition can be combined with a solution and with diluting, dispersing and/or surface active agents.

Formulations for aerosol administration include formulations designed for intranasal administration. An active ingredient can be provided in a pressurized pack with a suitable propellant such as a chlorofluorocarbon (CFC) (e.g., dichlorodifluoromethane, trichlorofluoromethane, or dichlorotetrafluoroethane), carbon dioxide, or other suitable gas. An aerosol may also contain a surfactant such as lecithin. A dose of drug may be controlled by a metered valve. Alternatively active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. A powder composition may be presented in unit dose form for example in capsules or cartridges of e.g., gelatine or blister packs from which the powder may be administered by means of a device.

A pharmaceutical composition formulated for intranasal administration comprises about 0.001 to about 5000 IU of KLK1, or a variant, or an active fragment thereof, optionally, further comprising a pharmaceutically acceptable excipient. Formulations suitable for oral administration include liquids, pills, solution, tablets, sustained release capsules, enteric coated capsules or syrups. A pharmaceutical composition formulated for oral administration comprises about 0.001 to 1000 IU of KLK1, or a variant or an active fragment thereof, optionally further comprising a pharmaceutically acceptable excipient. In an embodiment, a pharmaceutical composition formulated for oral administration comprises at least about 1.0 µg/ml of KLK1, or a variant or an active fragment thereof, optionally further comprising a pharmaceutically acceptable excipient. A composition can comprise at least about 2.0 µg/ml, 2.5 µg/ml, 5 µg/ml, 7.5 µg/ml, or 10 µg/ml of KLK1, or a variant or an active fragment thereof.

Pharmaceutical Compositions Useful for Intranasal Administration and Uses Thereof An aspect of the invention includes a composition formulated for intranasal administration comprising about 0.001 to about 5000 IU of KLK1, or a variant or an active fragment thereof, optionally comprising a pharmaceutically acceptable excipient.

A composition can be administered to the nasal cavity of a human or other mammal to diseased areas of the brain by means of the olfactory neural pathway. The method may employ a pharmaceutical composition capable of transporting KLK1 to diseased neurons of the brain.

A method of the invention can deliver of compounds to afflicted areas of the brain through transneuronal retrograde and anterograde transport mechanisms. Delivery of neurologic agents to the brain by that transport system can be achieved in several ways. One technique comprises delivering a neurologic agent alone to the nasal cavity. In this instance, chemical characteristics of KLK1 can facilitate its transport to diseased neurons in the brain. Peripheral nerve cells of the olfactory neural pathway can be utilized in order to deliver KLK1 to damaged neurons in those regions of the brain that are connected to the olfactory bulb.

KLK1 can be administered to the nasal cavity alone or in combination with a second therapeutic compound useful in treating Alzheimer's disease. KLK1 can be combined with a carrier and/or other adjuvants to form a pharmaceutical composition. Potential adjuvants include, but are not limited to, GM-1, phosphatidylserine (PS), and emulsifiers such as polysorbate 80. Further supplementary substances include, but are not limited to, lipophilic substances such as gangliosides and phosphatidylserine (PS).

A method of the invention delivers KLK1 to the nasal cavity of a mammal. It is preferred that KLK1 be delivered to the olfactory area in the upper third of the nasal cavity and particularly to the olfactory epithelium to promote transport of the agent into the peripheral olfactory neurons rather than the capillaries within the respiratory epithelium. Thereby KLK1 is transported by means of the nervous system to the brain and damaged neurons in the brain.

In one embodiment of the method of the invention, KLK1 can be combined with micelles comprised of lipophilic substances. Such micelles can modify the permeability of the nasal membrane and enhance absorption of the agent. Lipophilic micelles include gangliosides, particularly GM-1 ganglioside, and phosphatidylserine (PS).

Once KLK1 has crossed the olfactory epithelium, the invention further provides transport of KLK1 along the olfactory neural pathway. KLK1 is capable of movement within the olfactory system. In particular, neurotrophic and neuritogenic substances have demonstrated ready incorporation into nerve cell membranes and an affinity for nerve cell receptor sites.

To deliver KLK1 to olfactory neurons, KLK1 alone or in combination with other substances as a pharmaceutical composition can be administered to the olfactory area located in the upper third of the nasal cavity. The composition can be dispensed intranasally as a powdered or liquid nasal spray, nose drops, a gel or ointment, through a tube or catheter, by syringe, by packtail, by pledget, or by submucosal infusion.

A pharmaceutical composition for intranasal administration may be formulated as a powder, granules, solution, ointment, cream, aerosol, powder, or drops. A solution may be sterile, isotonic or hypotonic, and otherwise suitable for administration by injection or other means. In addition to KLK1, a solution may contain appropriate adjuvants, buffers, preservatives and salts. Powder or granular forms of a pharmaceutical composition may be combined with a solution and with diluting, dispersing and/or surface active agents. Solutions such as nose drops may contain antioxidants, buffers, and the like.

The olfactory system provides a direct connection between the outside environment and the brain thus providing quick and ready delivery of KLK1 for treating Alzheimer's disease and amnesiac mild cognitive impairment. Moreover, means of applying a pharmaceutical composition intranasally can be in a variety of forms such as a powder, spray, or nose drops that obviates intravenous or intramuscular injections and simplifies administration of therapeutic medications.

The invention will be described with reference to various specific and preferred embodiments and techniques. However, it should be understood that many variations and modifications may be made while remaining within the spirit and scope of the invention.

EXAMPLES

Example 1

In Vitro Amyloid Protein Cleavage Assay

Preparation of Fibrils

Synthetic human amyloid protein A$\beta$1-42 or A$\beta$1-40 was dissolved in dimethyl sulfoxide (DMSO) (Sigma, St. Louis, Mo.) to a concentration of 5 mM, and is then diluted in MilliQ® water to a final concentration of 25 mM immediately prior to use. To prepare amyloid fibrils (fA$\beta$) 5 mM A$\beta$1-42 or A$\beta$1-40 in DMSO was diluted in 10 mM HCl to 100 μM (for A$\beta$1-42) or 200 mM (for A$\beta$1-40), vortexed for 30 s, and was incubated at 37° C. for 5 days.

Digestion of Fibrils:

KLK1 (Sigma) was used for digestion reactions in the following buffers: ECE, 0.1 M MES, 0.1 M NaCl (pH 6.0); IDE, 50 mM Tris, 1 M NaCl (pH 7.5); NEP, 0.1 M MES (pH 6.5); and MMP-9, 50 mM Tris-HCl (pH 7.5), 10 mM CaCl$_2$, 150 mM NaCl, 0.05% Brij 35. It was incubated at 37° C. for 4 h to 5 days. After digestion, the reaction was analyzed by mass spectroscopy.

Figure 2:
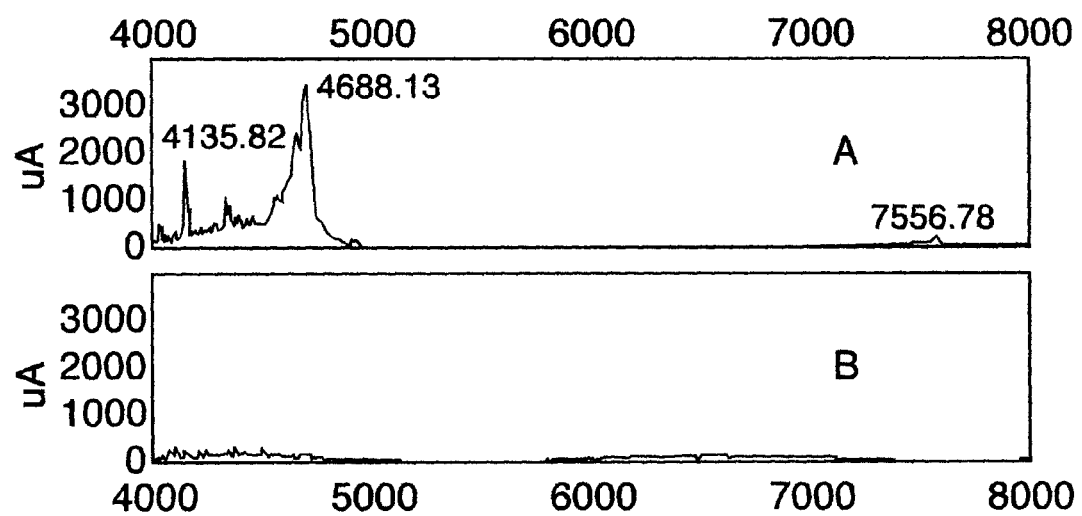
FIG. 2 is mass spectra showing tissue kallikrein cleavage of soluble amyloid in vitro. A) soluble Aβ alone; and B) soluble Aβ and KLK1.

Analysis of Fibril Cleavage:

The samples were added to 50 mM glycine (pH 9.2)/2 mM thioflavin T (ThT) (Sigma) at a final volume of up to 2 ml. Fluorescence was measured spectrophotometrically at excitation and emission wavelengths of 435 and 485 nm, respectively. Analysis indicates that KLK1 cleaves amyloid fibrils (FIG. 1) and soluble amyloid oligomers (FIG. 2). In FIG. 1, panel A shows A$\beta$ alone, where there was a large clump of amyloid fibril and no appearance of small fragments. Panel B shows KLK1 alone where there were no significant small peptide fragments. However, in panel C, there is a clear peak at about 2423 M/Z (mass to charge ration), which is an indication of cleavage. In FIG. 2, panel A shows that soluble amyloid have visible peaks between about 4000 to 5000 M/Z. In panel B, there are no visible peaks when KLK1 was added to soluble amyloid. This indicates that KLK1 cleaved the soluble amyloid into smaller fragments. The results show that KLK1 cleaves fibrils and soluble forms of amyloid, suggesting KLK1 is be useful in treating diseases associated with fibril plaques and soluble amyloid Example 2

Effect of Tissue Kallikrein on A$\beta_{1-42}$ Toxicity in Rat Mixed Cortical Cultures Whether pre-treatment with tissue kallikrein protects rat mixed cortical cultures against exposure to human amyloid beta peptide (Aβ$_{1-42}$) was investigated. Cell death was analyzed by LDH-release, an indication of necrosis, and cell viability was also analyzed by neuronal cell count. First (Study Arm A), tissue kallikrein was added to the cells only prior to the Aβ$_{1-42}$ insult (at −24 h and at −30 min). Whereas in the second part (Study Arm B), tissue kallikrein was added to the cells prior to (−30 min) and also at +24 h after the Aβ$_{1-42}$ insult. At the +24 h time point, cell culture media were not changed (tissue kallikrein or corresponding amount of vehicle was added to the wells), whereas at −24 h and −30 min time point cell culture media were changed.

Methods

RNAC Cell Culture. Mixed cortical cultures were prepared from E18 Wistar rat embryos (National Animal Center, Kuopio, Finland). The cortices were dissected out, and the tissue cut to small pieces. The cells were separated by 15-min incubation with DNase and papain. The cells were collected by centrifugation (1500 rpm, 5 min). The tissue was triturated with a pipette and the cells were plated on poly-L-lysine-coated 48-well plates, 300,000 cells/cm$^2$, in MEM (2 g/L glucose) supplemented with 2 mM glutamine, 0.1 μg/ml gentamicin, 10% heat-inactivated fetal bovine serum (FBS-HI) and 10% heat-inactivated horse serum (HS-HI). After 3-4 h, the media were changed to MEM (2 g/L glucose) supplemented with 2 mM glutamine, 0.1 μg/ml gentamicin, 5% HS-HI. After three days in vitro, media containing MEM (2 g/L glucose) supplemented with glutamine, gentamicin, and 5% of both sera were changed to the cells. On day 6 in vitro, the unwanted cell division was inhibited by adding cytosine arabinoside (10 μM final concentration) for 24 h. The cultures were refed with MEM (2 g/L glucose) supplemented with glutamine, gentamicin, and 5% HS-HI before experiments.

Aβ$_{1-42}$ Exposure. Tissue kallikrein (SEQ ID NO:1) was dissolved and further diluted in MEM supplemented with glucose, glutamine, gentamicin, and 5% HS-HI. As a control for total neuronal death, 300 μM N-methyl-D-aspartic acid (NMDA) for 48 h was used, and 10 μM Aβ$_{1-42}$ for 48 h was used to induce approximately 30-50% cell death. Wells treated with media only served as 0-control. Tissue kallikrein or vehicle was pipetted to the cells −24 h and −30 min before adding 10 μM Aβ$_{1-42}$ (final concentration). Tissue kallikrein or vehicle was again pipetted to the cells at +24 h after exposure.

LDH Measurement. After 48 h, the culture media of all wells were collected, and possible cell debris was removed by centrifugation (13,000 rpm for 3 min). A 100 μl aliquot was pipetted into a microtiter plate as duplicates, and equal amount of LDH reagent was pipetted to the wells. The absorbance at 340 nm was measured immediately using a 3 min kinetic measurement protocol in Multiskan ELISA reader (Labsystems, Finland). The change in absorbance/min was determined, which was directly proportional to the released LDH. The remaining supernatant (50 μl) was snap-frozen in dry ice for storage.

Immunocytochemistry for Neuronal Survival. For neuronal counts, the cultures were fixed with 4% paraformaldehyde in 0.01 M PBS for 30 min and washed twice with PBS. The fixed cells were first permeabilized, and non-specific binding blocked by 30 min incubation with blocking buffer containing 1% bovine serum albumin and 0.3% Triton® X-100 in PBS. Anti-neuronal nuclei antibody (anti-NeuN, dilution 1:500, Chemicon, Temecula, Calif.) was used as the primary antibody. The cells were incubated with the primary antibody for 48 h, followed by incubation with a biotinylated secondary antibody (1:200, Vector Labs) for 2 h, and the avidin-biotin-peroxidase complex (ABC-reagent, 1:200, Vector ABC Elite Kit, Vector Labs) for 2 h. The positive cells were visualized using Ni-enhanced DAB as a substrate (DAB Substrate kit, Vector Labs). The NeuN immunopositive neurons were counted using a light microscope. Altogether, 2 fields of each well were counted. The results are shown as percent viable neurons.

Data Analysis. The number of wells per compound concentration used was 6 (n=6). Five concentrations of Tissue kallikrein were studied (0.001, 0.01, 0.1, 1, 10 μg/ml) in both study arms. Statistical analysis was performed using StatsDirect statistical software. The values were analyzed by one-way ANOVA followed by Dunnet's test (comparison to the vehicle-treated group). Results are presented as mean±standard deviation (SD) and differences are considered to be statistically significant at the $P<0.05$ level.

Results

Figure 3:
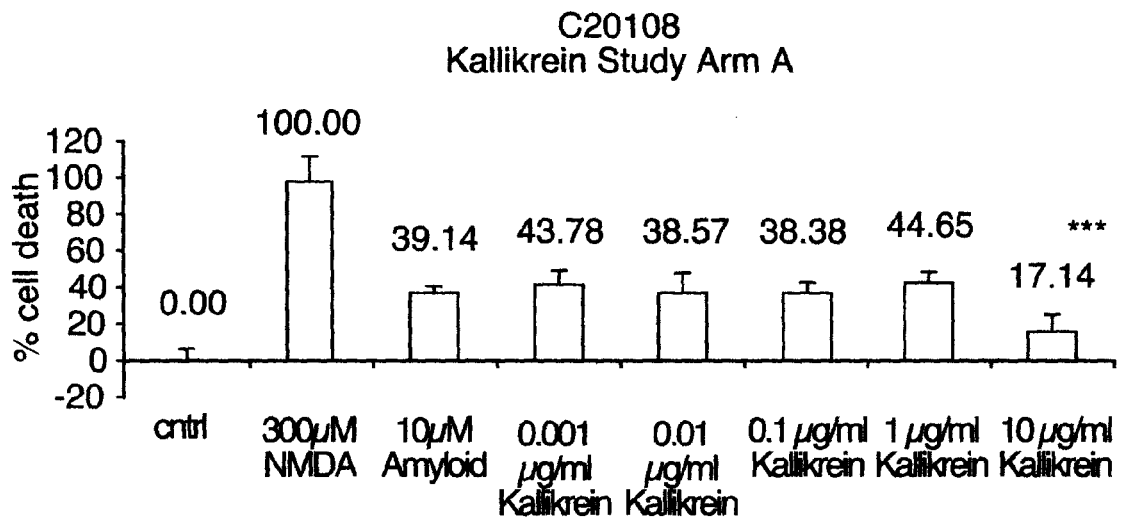
FIG. 3 is a bar graph showing LDH measurement of tissue kallikrein treated rat mixed cortical cultures (RMCC). Tissue kallikrein was added to the cells only prior to the $A\beta_{1-42}$ insult (10 μM final concentration) at −24 h and at −30 min. The data are presented as percent increase compared to baseline values (10 μM $A\beta_{1-42}$ wells), 300 μM NMDA set as 100%, and data shown as mean+SD. ***p<0.0001 (1-way ANOVA) represents statistically significant difference compared to the vehicle (=10 μM $A\beta_{1-42}$) group.
Figure 4:
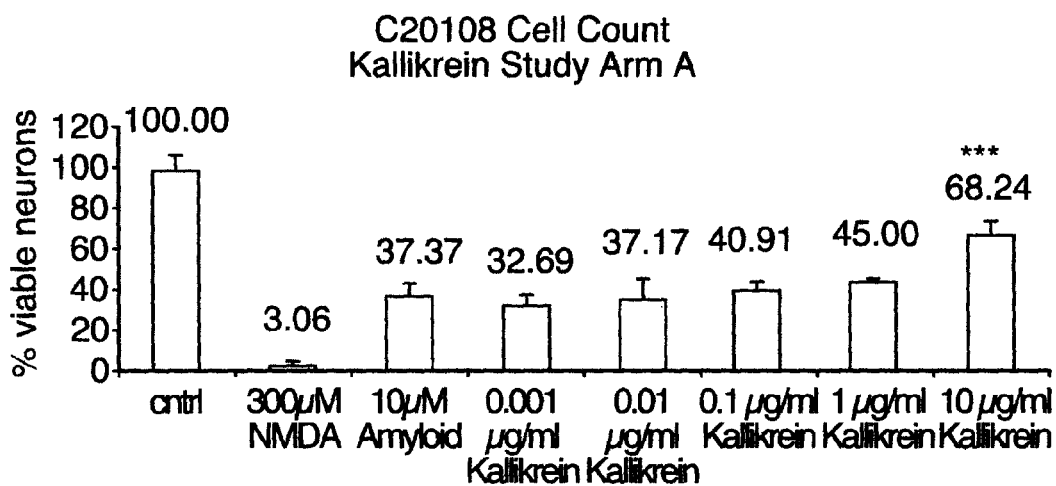
FIG. 4 is a bar graph showing neuronal survival of tissue kallikrein treated rat mixed cortical cultures (RMCC). Tissue kallikrein was added to the cells only prior to the $A\beta_{1-42}$ insult (10 µM final concentration) at −24 h and at −30 min. The number of NeuN-immunoreactive neurons was counted 48 h after 10 µM $A\beta_{1-42}$ exposure. The data are presented as percent viable neurons, as mean+SD. ***p<0.0001 (1-way ANOVA) represents statistically significant difference compared to vehicle (=10 µM $A\beta_{1-42}$) group.

Tissue kallikrein Results. (Study Arm A) Tissue kallikrein was added to the cells only prior to the Aβ$_{1-42}$ insult (10 μM final concentration) at −24 h and at −30 min. At −24 h and −30 min time point cell culture media were changed. The Aβ$_{1-42}$ insult in the absence of tissue kallikrein resulted in a 39.14% LDH release when compared to the 100% LDH release caused by the NMDA control. Tissue kallikrein at concentrations of 0.001 μg/ml, 0.01 μg/ml, 0.1 μg/ml, and 1.0 μg/ml did not alter LDH release following the Aβ$_{1-42}$ insult (FIG. 3). However, 10 μg/ml tissue kallikrein significantly reduced LDH release. Likewise, lower concentrations of tissue kallikrein did not affect cell counts (survival) after the Aβ$_{1-42}$ insult (FIG. 4). Tissue kallikrein at 1.0 μg/ml and 10 μg/ml provided protection where RMCC counts increased compared to the RMCC challenged with Aβ$_{1-42}$ and without tissue kallikrein. The protection provided by 10 μg/ml was statistically significant.

Figure 5:
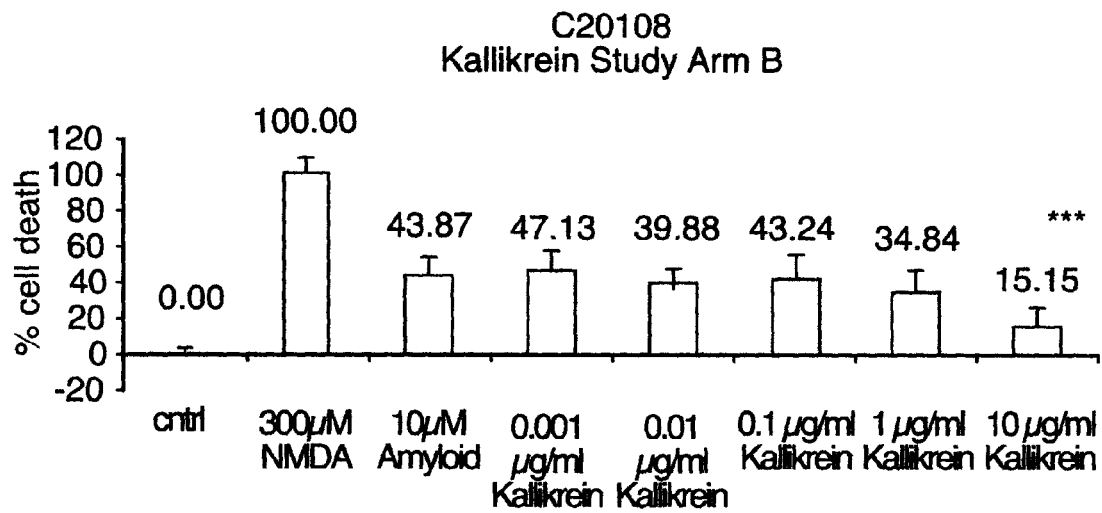
FIG. 5 is a bar graph showing LDH measurement of tissue kallikrein treated rat mixed cortical cultures (RMCC). Tissue kallikrein was added to the cells prior to (−30 min) and also at +24 h after the $A\beta_{1-42}$ insult. The data are presented as percent increase compared to baseline values (10 µM $A\beta_{1-42}$ wells), 300 µM NMDA set as 100%, and data shown as mean+SD. ***p=0.0002 (1-way ANOVA) represents statistically significant difference compared to the vehicle (=10 µM $A\beta_{1-42}$) group.
Figure 6:
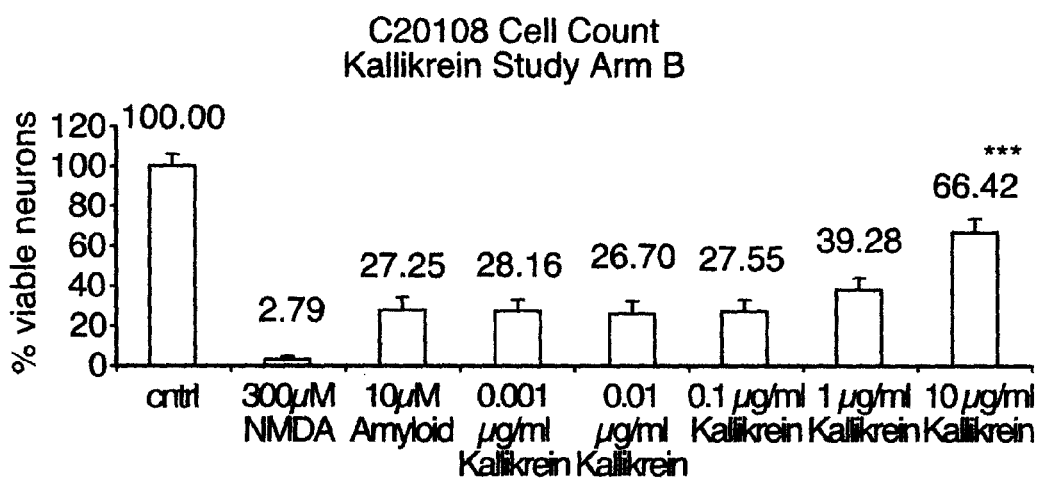
FIG. 6 is a bar graph showing neuronal survival of tissue kallikrein treated rat mixed cortical cultures (RMCC). Tissue kallikrein was added to the cells 30 min prior to and also at 24 h after the $A\beta_{1-42}$ insult. The number of NeuN-immunoreactive neurons was counted 48 h after 10 µM $A\beta_{1-42}$ exposure. The data are presented as percent viable neurons, as mean+SD. ***p<0.0001 (1-way ANOVA) represents statistically significant difference compared to vehicle (=10 µM $A\beta_{1-42}$) group.

(Study Arm B) Tissue kallikrein was added to the cells prior to (−30 min) and also at +24 h after the Mβ$_{1-42}$ insult (10 μM final concentration). At +24 h time point, cell culture media were not changed (tissue kallikrein or corresponding amount of vehicle was added to the wells), whereas at −30 min time point cell culture media were changed. The Aβ$_{1-42}$ insult in the absence of tissue kallikrein resulted in a 43.87% LDH release when compared to the 100% LDH release caused by the NMDA control. Tissue kallikrein at concentrations of 0.001 μg/ml, 0.01 μg/ml, and 0.1 μg/ml did not alter LDH release following the Aβ$_{1-42}$ insult (FIG. 5). However, 1.0 μg/ml and 10 μg/ml tissue kallikrein reduced LDH release, and the 10 μg/ml administration of tissue kallikrein produced a statistically significant reduction of LDH release. Likewise, lower concentrations of tissue kallikrein did not affect cell counts (survival) after the Aβ$_{1-42}$ insult (FIG. 6). Increases in cell counts can be seen when 1.0 μg/ml and 10 μg/ml of tissue kallikrein was applied to the RMCC compared to the RMCC challenged with Aβ$_{1-42}$ and without tissue kallikrein. The protection provided by 10 μg/ml was statistically significant.

Summary

Tissue kallikrein at 10 μg/ml decreased Aβ$_{1-42}$-induced neuronal death in both tissue kallikrein administration schemes ((Study Arm A) and (Study Arm B) above), as determined by measurement of both LDH release and neuronal cell counting (statistically significant in both tests). These results suggest that pretreatment (at −24 h and at −30 min) and combined pre-(−30 min) and post-(+24 h) treatment with tissue kallikrein protects rat cortical cultures against Aβ$_{1-42}$ induced cell death.

Example 3

Figure 7:
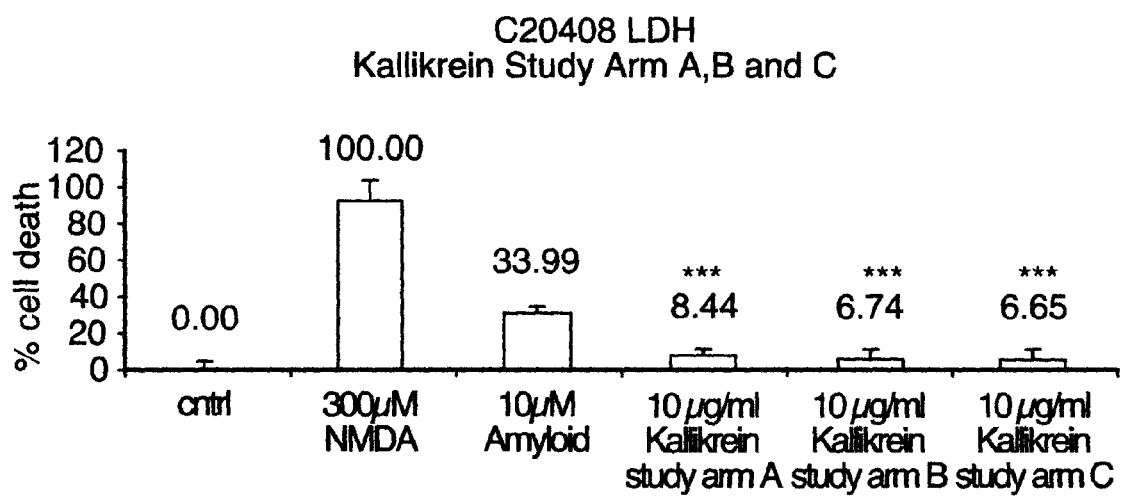
FIG. 7 is a bar graph showing LDH measurement of 10 µg/ml tissue kallikrein treated rat mixed cortical cultures (RMCC). Kallikrien was added to the cells 24 h and 30 min prior to the $A\beta_{1-42}$ insult (Study Arm A), was added to the cells 30 min prior to and also at 24 h after the $A\beta_{1-42}$ insult (Study Arm B) and was added to the cells prior to (−24 h and −30 min) and also at 24 hours after the $A\beta_{1-42}$ insult (Study Arm C). The data are presented as percent increase compared to baseline values (10 µM $A\beta_{1-42}$ wells), 300 µM NMDA set as 100%, and data shown as mean+SD. ***p<0.0001 (1-way ANOVA) represents statistically significant difference compared to the vehicle (=10 µM $A\beta_{1-42}$) group.

Effect of Tissue Kallikrein at 10 μg/ml on $A\beta_{1-42}$ Toxicity in Rat Mixed Cortical Cultures Using Different Treatment Arms The effect of 10 μg/ml kallikrein on $A\beta_{1-42}$ toxicity in rat mixed cortical cultures (RMCC) was also tested. The methods use to test the effect of kallikrein were the same as those used to test tissue kallikrein in Example 2 Three different administration schemes of kallikrein (10 μg/ml) to RMCC were tested—Study Arm A) at 24 h and 30 min prior to $A\beta_{1-42}$ insult, Study Arm B) at 30 min prior to and also at 24 h after $A\beta_{1-42}$ insult, and Study Arm C) at 24 h and 30 min prior to and also at 24 h after $A\beta_{1-42}$ insult. The results are presented in FIG. 7. Treatment of RMCC with 10 μg/ml of kallikrein did provide protection from the $A\beta_{1-42}$ insult as seen by a statistically significant reduction of LDH release in all three treatment arms. These results suggest that pretreatment (at −24 h and at −30 min), combined pre-(−30 min) and post-(+24 h), and combined pre-(−24 h and at −30 min) and post-(+24H) treatment with a fixed concentration of tissue kallikrein (10 μg/ml) protects rat cortical cultures against $A\beta_{1-42}$ induced cell death.

Example 4

Figure 8:
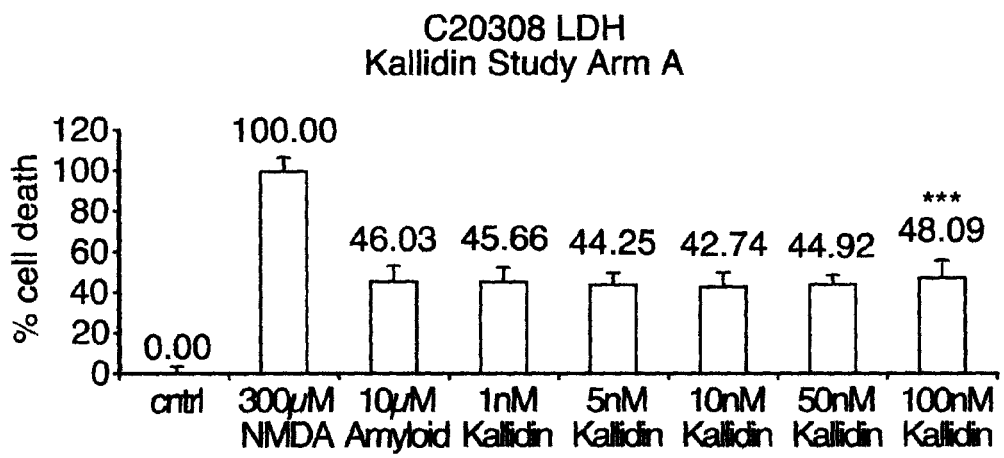
FIG. 8 is a bar graph showing LDH measurement of kallidin treated rat mixed cortical cultures (RMCC). Kallidin was added to the cells 24 h and 30 min prior to the $A\beta_{1-42}$ insult. The data are presented as percent increase compared to baseline values (10 µM $A\beta_{1-42}$ wells), 300 µM NMDA set as 100%, and data shown as mean+SD.
Figure 9:
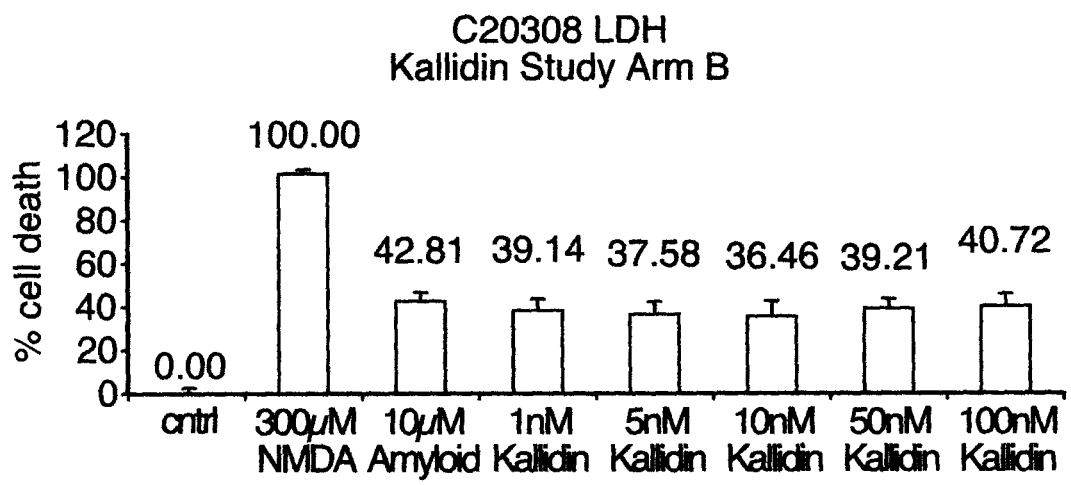
FIG. 9 is a bar graph showing LDH measurement of kallidin treated rat mixed cortical cultures (RMCC) Kallidin was added to the cells 30 min prior to and also at 24 h after the $A\beta_{1-42}$ insult. The data are presented as percent increase compared to baseline values (10 µM $A\beta_{1-42}$ wells), 300 µM NMDA set as 100%, and data shown as mean+SD.
Figure 10:
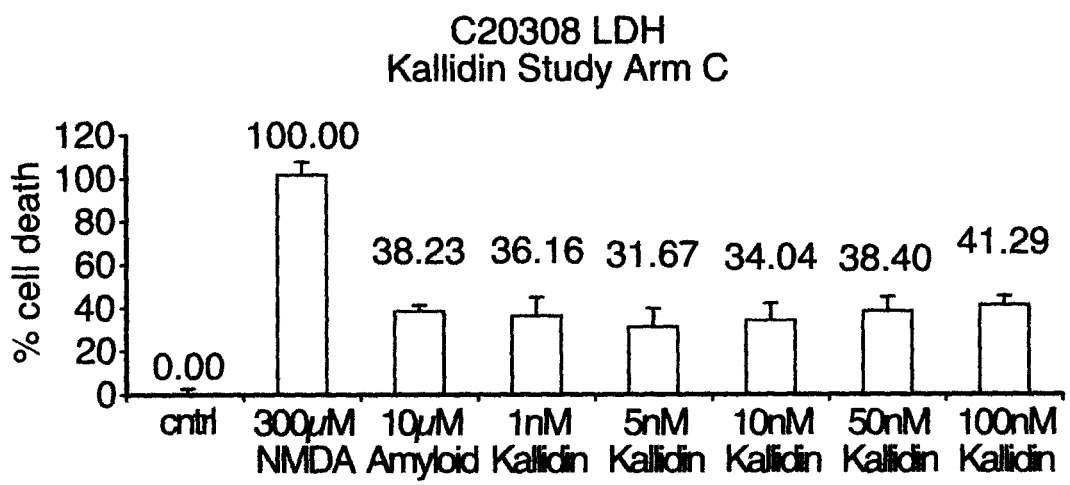
FIG. 10 is a bar graph showing LDH measurement of kallidin treated rat mixed cortical cultures (RMCC). Kallidin was added to the cells prior to (−24 h and −30 min) and also at 24 hours after the $A\beta_{1-42}$ insult. The data are presented as percent increase compared to baseline values (10 µM $A\beta_{1-42}$ wells), 300 µM NMDA set as 100%, and data shown as mean+SD.
Figure 11:
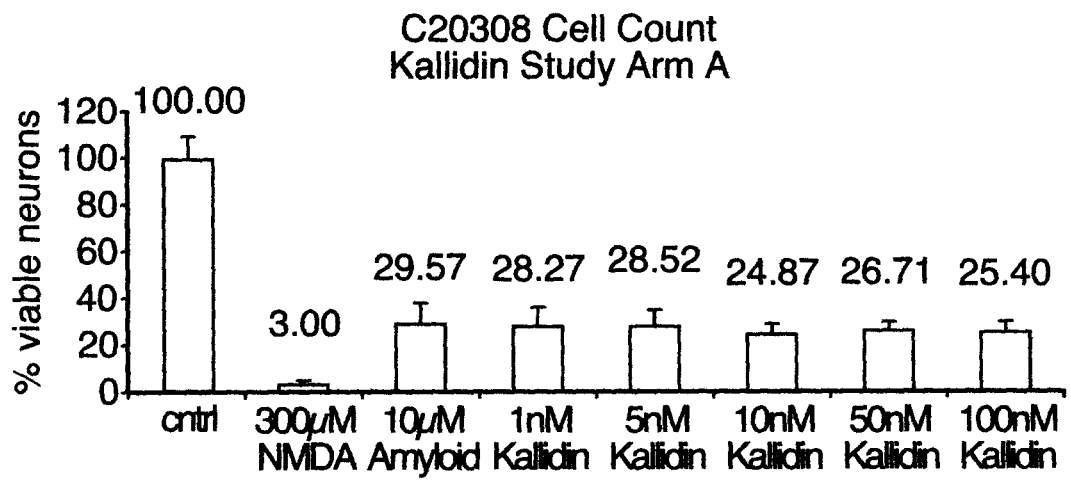
FIG. 11 is a bar graph showing cell count measurement of kallidin treated rat mixed cortical cultures (RMCC). Kallidin was added to the cells 24 h and 30 min prior to the $A\beta_{1-42}$ insult. The number of NeuN-immunoreactive neurons was counted 48 h after 10 µM $A\beta_{1-42}$ exposure. The data are presented as percentage of viable neurons compared to baseline values (10 µM $A\beta_{1-42}$ wells), 300 µM NMDA set as 100%, and data shown as mean+SD.
Figure 12:
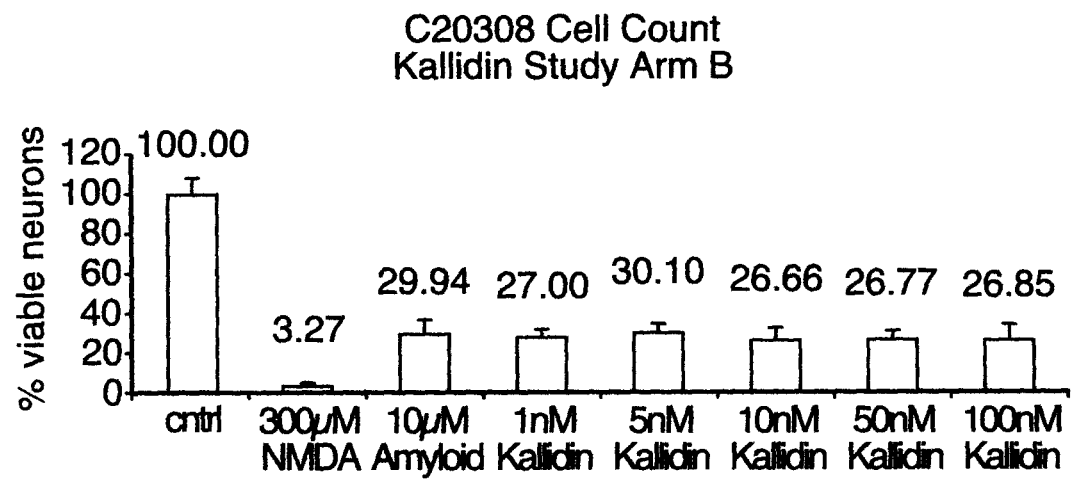
FIG. 12 is a bar graph showing cell count measurement of kallidin treated rat mixed cortical cultures (RMCC) Kallidin was added to the cells 30 min prior to and also at 24 h after the $A\beta_{1-42}$ insult. The number of NeuN-immunoreactive neurons was counted 48 h after 10 µM $A\beta_{1-42}$ exposure. The data are presented as percentage of viable neurons compared to baseline values (10 µM $A\beta_{1-42}$ wells), 300 µM NMDA set as 100%, and data shown as mean+SD.
Figure 13:
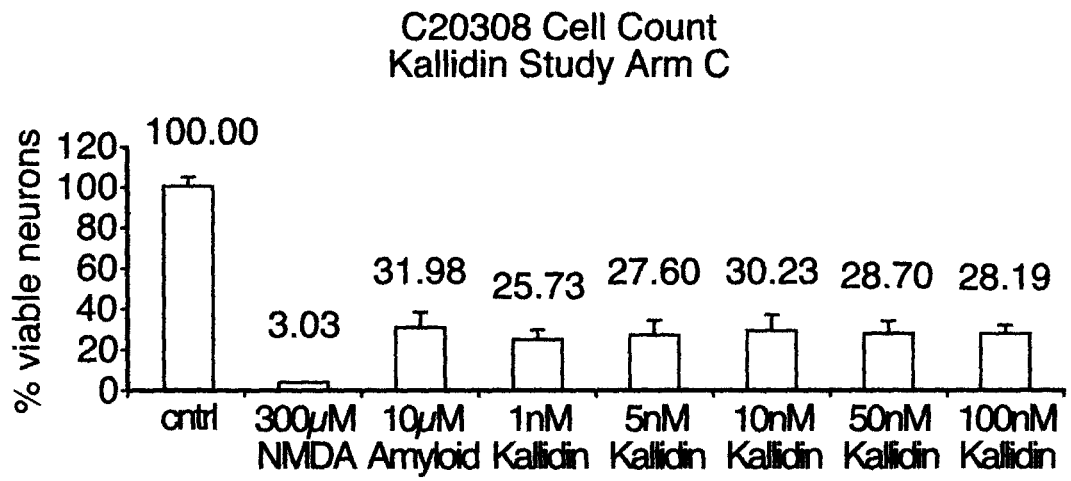
FIG. 13 is a bar graph showing cell count measurement of kallidin treated rat mixed cortical cultures (RMCC). Kallidin was added to the cells prior to (−24 h and −30 min) and also at 24 hours after the $A\beta_{1-42}$ insult. The number of NeuN-immunoreactive neurons was counted 48 h after 10 µM $A\beta_{1-42}$ exposure. The data are presented as percentage of viable neurons compared to baseline values (10 µM $A\beta_{1-42}$ wells), 300 µM NMDA set as 100%, and data shown as mean+SD.

Effect of Kallidin (1 nM-100 nM) on $A\beta_{1-42}$ Toxicity in Rat Mixed Cortical Cultures The effect of kallidin on $A\beta_{1-42}$ toxicity in rat mixed cortical cultures (RMCC) was also tested. The methods used to test the effect of kallidin were the same as those used to test tissue kallikrein in Example 2. Three different administration schemes of kallidin to RMCC were tested—Study Arm A) at 24 h and 30 min prior to $A\beta_{1-42}$ insult, Study Arm B) at 30 min prior to and also at 24 h after $A\beta_{1-42}$ insult, and Study Arm C) at 24 h and 30 min prior to and also at 24 h after $A\beta_{1-42}$ insult. Treatment of RMCC with kallidin (1 nM, 5 nM, 10 nM, 50 nM, and 100 nM) did not alter LDH release following $A\beta_{1-42}$ insult (FIGS. 8-10) and did not affect cell counts (survival) following $A\beta_{1-42}$ insult (FIGS. 11-13) in study arm A, B, or C. This is counter-intuitive since kallidin activates the bradykinin B2 receptor, which leads to increased expression of MMP-9, which can cleave amyloid. One would hypothesize that increasing MMP-9 by kallidin administration would lead to increased amyloid cleavage and protection from $A\beta_{1-42}$ induced cell death.

Example 5

Figure 14:
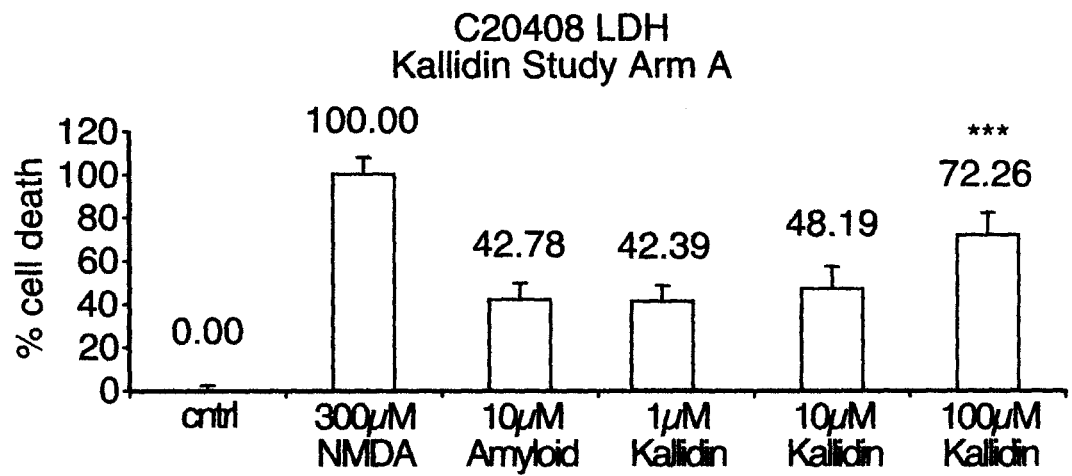
FIG. 14 is a bar graph showing LDH measurement of kallidin treated rat mixed cortical cultures (RMCC). Kallidin was added to the cells 24 h and 30 min prior to the $A\beta_{1-42}$ insult. The data are presented as percent increase compared to baseline values (10 µM $A\beta_{1-42}$ wells), 300 µM NMDA set as 100%, and data shown as mean+SD. ***p<0.0001 (1-way ANOVA) represents statistically significant difference compared to the vehicle (=10 µM $A\beta_{1-42}$) group.
Figure 15:
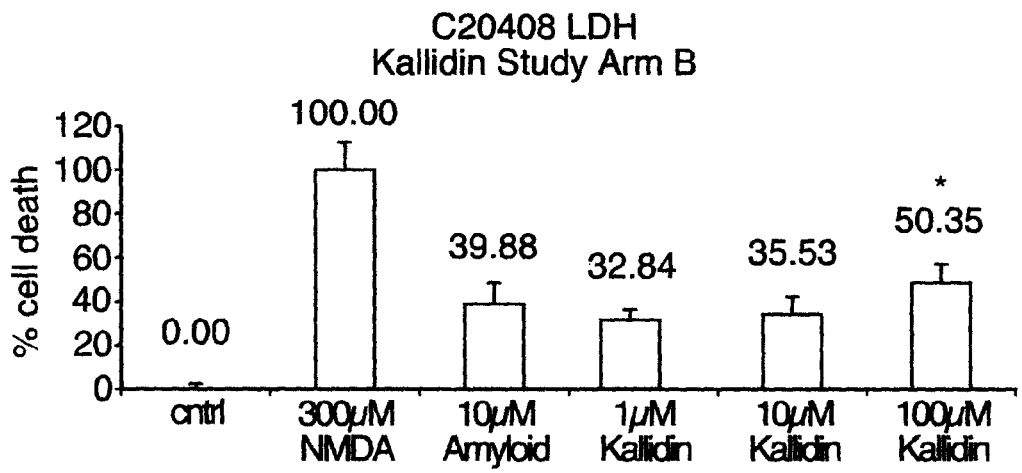
FIG. 15 is a bar graph showing LDH measurement of kallidin treated rat mixed cortical cultures (RMCC) Kallidin was added to the cells 30 min prior to and also at 24 h after the $A\beta_{1-42}$ insult. The data are presented as percent increase compared to baseline values (10 µM $A\beta_{1-42}$ wells), 300 µM NMDA set as 100%, and data shown as mean+SD. *p<0.05 (1-way ANOVA) represents statistically significant difference compared to the vehicle (=10 µM $A\beta_{1-42}$) group.
Figure 16:
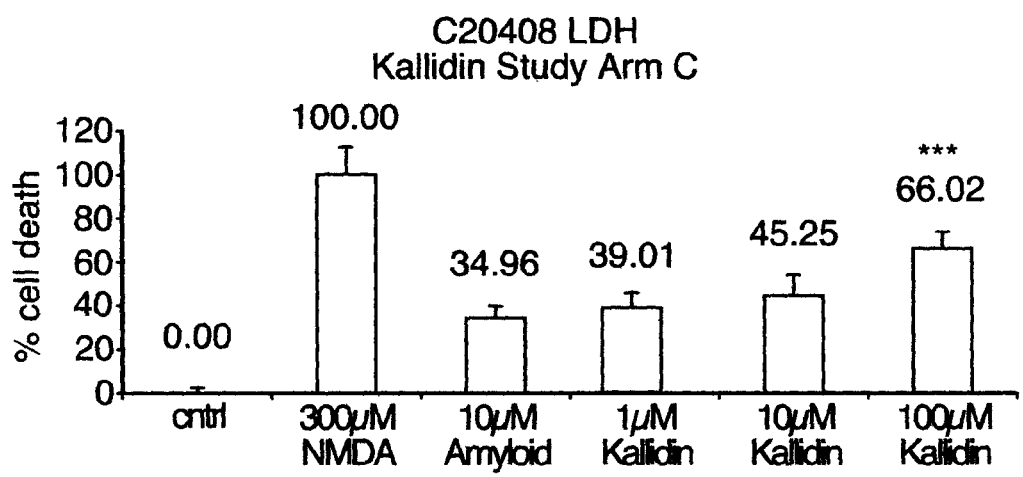
FIG. 16 is a bar graph showing LDH measurement of kallidin treated rat mixed cortical cultures (RMCC). Kallidin was added to the cells prior to (−24 h and −30 min) and also at 24 hours after the $A\beta_{1-42}$ insult. The data are presented as percent increase compared to baseline values (10 µM $A\beta_{1-42}$ wells), 300 µM NMDA set as 100%, and data shown as mean+SD. ***p<0.0001 (1-way ANOVA) represents statistically significant difference compared to the vehicle (=10 µM $A\beta_{1-42}$) group.

Effect of Kallidin (1 μM-100 μM) on $A\beta_{1-42}$ Toxicity in Rat Mixed Cortical Cultures The effect of kallidin on $A\beta_{1-42}$ toxicity in rat mixed cortical cultures (RMCC) was retested following the Example 4 method and study arms. The results are presented in study arm A, B, and C in FIGS. 14-16. Treatment of RMCC with kallidin at 1 μM and 10 μM did alter LDH release in study arm A, B, or C following $A\beta_{1-42}$ insult. However, rather unexpectedly, treatment of RMCC with kallidin at 100 μM significantly potentated cell death following $A\beta_{1-42}$ insult compared to $A\beta_{1-42}$ insult alone suggesting at this concentration kallidin is toxic to RMCC. This is counter-intuitive since kallidin activates the bradykinin B2 receptor, which leads to increased expression of MMP-9, which can cleave amyloid. One would hypothesize that increasing MMP-9 by kallidin administration would lead to increased amyloid cleavage and protection from $A\beta_{1-42}$ induced cell death.

Example 6

Pharmacokinetic Study of Intranasal Tissue Kallikrein

The purpose of this study was to quantify the amount of tissue kallikrein (KLK1) reaching the central nervous system and peripheral tissues after intranasal administration to anesthetized rats. At 30 min after KLK1 administration, animals were transcardially perfused with ice-cold saline followed by paraformaldehyde fixative and tissues were dissected. The amount of radiolabeled KLK1 in each tissue sample was quantified by gamma counting and tissue concentrations were calculated using tissue weight and gamma counting of standards of the dosing solutions Animals Adult male Sprague Dawley rats (n=10, mean 335.4 g±4.57 g SE) were used for this study. Animals were group housed in the Regions Hospital Animal Care Facility with free access to food and water. Animals were kept on a 12 h light cycle. All experimental procedures were approved by the Animal Care and Use Committee at Regions Hospital under IACUC protocol number 08-022.

Formulations

Tissue kallikrein was sent to Perkin-Elmer for $^{125}$I-labelling (Quote NEX-084, lot C1541583). Non-labeled KLK1 from Sigma (cat#K3627-1KU, lot 018K1441) was also used. Non-labeled KLK1 was dissolved in 1×PBS (10×PBS, Sigma, cat #P5493, lot 027K8405 diluted in sterile water). The average dose was 48.1 μL, 75 μCi, and 2.6 mg.

Anesthesia a. Prior to anesthesia, each rat was weighed.
  b. An anesthesia cocktail was prepared and full, half, and quarter anesthesia doses were calculated according to the animal's weight with a full dose containing 30 mg/kg ketamine, 6 mg/kg xylazine, and 1 mg/kg acepromazine.
  c. A 1-cc syringe fitted with a 25 G or 27 G, ½ inch needle was assembled and a full dose was drawn into the syringe for injection.
  d. Rats were restrained in a towel as follows. Rats were placed ventral side down in the middle of a hand towel. The towel was then wrapped around the head and shoulders to restrain. Wrapped animals remained ventral side down while the left hind leg was located.
  e. The left hind leg was drawn to the side and the needle was inserted just beneath the skin (subcutaneous) above the thigh. After ensuring that the needle was placed subcutaneously (and not intramuscularly), full doses were injected. Rats were placed in holding cages and the injection time noted. Animals should be under within 5 min.
  f. Anesthesia was monitored throughout the procedures by assessing reflexes using pinching of the hind paw or tail. If a reflex was present, a half or quarter dose booster was administered as necessary.
  g. During drug administration, animals received a half dose booster roughly 20-25 min after initial dose.

Intranasal Delivery of $^{125}$I-KLK1 a. Anesthetized rats were placed on their backs on a heating pad in a metal surgical tray. The heating pad was connected to a thermostat and was automatically regulated to maintain a 37° C. temperature based on continuous measurement from a rectal probe.

b. A 2"×2" gauze pad was rolled tightly into a pillow, taped together, and under the neck to maintain a correct neck position horizontal with the counter.
c. A lead impregnated shield was placed between the surgical tray and the experimenter for protection against radiation. The dose solution, pipette, pipette tips, and waste receptacle were arranged behind the shield for easy access.
d. A 6 μL drop was loaded into the pipette behind the shield.
e. A cotton swab covered in parafilm was used to occlude one naris completely (the flat part of the swab was pushed gently against the naris to prevent airflow), while the 6 μL drop was expelled slowly from the pipette (held at a 45° angle from the rat's midline), forming a drop on the pipette tip. The drop was lowered onto the open naris to be inhaled.
f. After two minutes, the alternate naris was occluded and a 6 μL drop was administered in the same fashion.
g. A drop was administered as described above every two minutes to alternating nares until a total of 8 drops was delivered (4 to each naris) over 14 min.
h. Delivered time of each drop was noted as well as any details regarding the animal's respiration or success of the delivery.

Three 3 μL it aliquots of each dosing solution were gamma counted to determine the measured specific activity Transcardial Perfusion a. Two min. prior to the desired end point time, anesthetized animals were laid flat on their backs in a metal surgical tray. The heating pad, rectal probe, and neck pillow were removed. Tape was used to secure the front limbs to the pan. The back of the pan was elevated slightly to allow blood to run away from the animal.
b. The sternum was exposed by cutting through the skin. The sternum was clamped with a hemostat and the rib cage was cut open laterally, exposing the diaphragm.
c. The diaphragm was cut laterally to expose the pleural cavity.
d. Surgical scissors were used to cut up the sides of the ribcage toward the armpits of the animal, creating a 'V' shaped incision exposing the heart.
e. The hemostat holding the sternum was taped above the head to hold the cavity open.
f. The heart was stabilized using the blunt forceps while a small cut was made into the left ventricle. A 1 cc-syringe with 18 G, 1" blunt needle was inserted into the left ventricle and approximately 0.1 mL of blood was removed and placed into a pre-weighed tube for gamma counting.
g. A second 18 G blunt needle attached to an extension set filled with 60 cc of saline was inserted through the left ventricle and into the aorta.
h. A large bulldog clamp was placed just above the heart on the aorta, securing the blunt needle in place.
i. The animal was perfused with 60 mL of saline followed by 360 mL of paraformaldehyde using a syringe pump at a rate of 15 mL/min.

Brain Dissection a. Throughout experimental procedures, strict precautions were followed to prevent radioactive contamination of animal tissues, surgical tools, and equipment. Geiger counters were placed at each work station to continuously screen tools, workspace, and staff. Personal protective equipment including double layered gloves, lab coats, eye protection, masks, and bouffant caps were worn at all times. Lead impregnated shields were used to minimize exposure to radiation. Radioactive monitoring badges were also worn by staff throughout experimental procedures to quantify exposure.
b. Immediately after collection, each tissue sample was placed into a pre-labeled and pre-weighed gamma tube for later measurement.
c. To remove the head, skin and muscle around the neck were cut with a scalpel just above the shoulder blades and a large pair of scissors used to decapitate the animal, cutting dorsal to ventral to avoid contamination from the trachea and esophagus.
d. To expose the brain, a midline incision was made on the dorsal side of the skull, then skin was peeled away, and a straight hemostat was used to break the bone, taking care to leave the dorsal dura attached.
e. Dorsal dura was collected.
f. To remove the brain from the skull, the head was inverted and a small spatula was used to free it from the cavity. The posterior optic nerve and trigeminal nerves were cut close to the brain. The brain was then placed into a clean Petri dish for dissection.
g. From the base of the skull, the ventral dura was collected by scraping a forceps on the ventral skull walls. The pituitary, optic chiasm, and trigeminal nerves were collected. The anterior portion of the trigeminal nerve consisted of the portion before the visible branch in the skull, while the remainder containing the trigeminal ganglion was considered as the posterior section. The head was then set aside and covered with a kim-wipe for later dissection.
h. Using surgical forceps, microscissors, and a 30 G needle, the basilar artery and circle of Willis were removed and placed onto pre-weighed paper (paper was used because of the small weight of this tissue). The needle was used to lift the vessels away from the brain, the forceps to grab hold, and the microscissors to make the cuts. This tissue was weighed immediately upon collection and then the entire paper was crumpled and placed into the bottom of tube).
i. Prior to placing the brain into the coronal matrix, the olfactory bulbs were cut off at the natural angle using a razor blade.
j. In the coronal brain matrix, a razor blade was inserted at the center of where optic chiasm was before removal to normalize each animal to the same location (bregma). Additional blades were placed every 2 mm from the first blade, resulting in 6×2 mm slices, 3 rostral to the optic chiasm and 3 caudal.
k. Blades were removed and tissues were dissected from each slice (1-6). Any remaining brain tissue from each slice was also.
l. The remaining section of cortex and hippocampus was dissected from the remaining brain tissue in the matrix and placed in respective tubes.
m. The upper cervical spinal cord was collected.
n. The remaining brain was then bisected along the midline and dissected into midbrain, pons, medulla, and cerebellum.
o. Returning to the head, the ventral side of the neck was cut anteriorly and skin peeled back exposing lymph nodes, salivary glands, and neck muscles.
p. The superficial nodes, deep cervical nodes, carotid arteries, and thyroid gland were dissected and cleared of connective tissue.
q. A razor blade was used to bisect the skull along the midline. The olfactory epithelium and respiratory epithelium were collected.

Body Dissection
- a. Immediately after collection, each tissue sample was placed into a pre-labeled and pre-weighed gamma tube for later measurement.
- a. Bodies were placed on their backs and a longitudinal cut using a scalpel was used to open the peritoneal cavity down to the bladder.
- b. 3 mm square samples of liver (superficial right lobe), kidney (left, tip), renal artery, spleen (tip), lung (right, top lobe), and heart were collected.
- c. Approximately 0.1-0.2 mL of urine was collected.
- d. Bodies were flipped over onto the stomach and a superficial incision was made down the length of the animal from shoulders to hips, following the spine. The skin was peeled away from the underlying tissue on both sides to expose the shoulder blades.
- e. Axillary nodes in the armpits were dissected and cleared of connective tissue.
- f. A piece of right deltoid muscle was collected (~3 mm$^2$).
- g. The muscles overlying the spine were scored with a scalpel. To expose the spinal cord, a small hemostat was inserted into the spinal column and used to chip away overlying vertebrae and tissues. A small spatula was used to loosen the cord from the spinal cavity and forceps used to remove it and place into a petri dish. The dura was peeled off of the cord using forceps. The cord was dissected into lower cervical, thoracic, and lumbar portions. The top ~2 mm of lower cervical segment was discarded.
- h. A 2 cm segment of trachea and esophagus was dissected from the body and connective tissues were removed. The top 0.5 cm (closest to the decapitation point) of each was discarded.

Tissue Counting

Pre-weighed gamma tubes containing samples were reweighed to determine tissue weight. Samples from all rats were counted using a COBRA II Auto-Gamma Counter (standard $^{125}$I protocol, 5 min count time, elevator position 1). The counter was normalized weekly to ensure a counting efficiency at or above 80%. For all rats, a background protocol was run in which the average measured background counts were automatically subtracted from the measured counts by the gamma counter.

Data Analysis and Calculations

Mean and standard error of the nM concentration of each tissue sample were calculated. Any value outside two standard deviations of the mean for each tissue was considered an outlier and removed from the data set. Outliers are denoted on an animal's data sheet by an 'X'.

The Excel spreadsheet auto calculated nM KLK1 concentrations for each tissue using the measured specific activity of dosing solutions, CPM of each tissue, and volume of each tissue (assuming 1 g=1 mL).

Sample Calculations nM concentration=(tissue counts in CPM)/(measured specific activity in cpm/fmol)/(tissue volume in mL)/(10$^3$ fmol/pmol)

Example: Olfactory bulbs for KLK 1

(4130 CPM)/(2.76 CPM/fmol)/(0.07734 mL)/(10$^3$ fmol/pmol)=19.35 pmol/mL=19.35 nM Results The results are summarized in Table 1.

Summary

KLK1 effectively reached target regions for treatment of neurologic disease including: 1) the frontal cortex, temporal cortex, hippocampus and other areas known to be involved in the neuropathology of Alzheimer's disease; 2) the cerebral blood vessel walls, the site of amyloid angiopathy in Alzheimer's disease; and 3) the cervical nodes of the lymphatic system, likely important for treatment of neuroinflammation.

TABLE 1

| | Intranasal kallikrien - nM concentrations - 30 min. end point-outliers removed | | | | | | | | | | | |
|---|---|---|---|---|---|---|---|---|---|---|---|---|
| | animal-1 | animal-2 | animal-3 | animal-4 | animal-5 | animal-6 | animal-13 | animal-14 | animal-15 | Animal-16 | Avg | SE |
| Volume Delivered (uL) | 47.2 | 47.2 | 47.3 | 47.3 | 47.6 | 47.6 | 48.7 | 48.7 | 49.4 | 49.4 | 48.1 | ±0.3 |
| uCi Delivered | 75.0 | 75.0 | 75.0 | 75.0 | 75.0 | 75.0 | 75.0 | 75.0 | 75.0 | 75.0 | 75.0 | ±0.0 |
| mg Delivered | 2.6 | 2.6 | 2.6 | 2.6 | 2.6 | 2.6 | 2.6 | 2.6 | 2.6 | 2.6 | 2.6 | ±0.0 |
| Olfactory Epithelium | 17,707.4 | 21,270.9 | 41,836.8 | 17,083.5 | 31,983.9 | 38,661.3 | 13,736.3 | 17,247.4 | 26,179.4 | 21,919.4 | 24,762.6 | ±3,065.8 |
| Respiratory Epithelium | 78,502.7 | 26,815.1 | 82,292.8 | 126,759.8 | 34,402.4 | 71,775.8 | 107,890.6 | 91,206.0 | 64,295.5 | 75,759.2 | 75,970.0 | ±9,530.7 |
| Anterior Trigeminal Nerve | 233.5 | 83.9 | 83.5 | 108.3 | X | 68.8 | 111.7 | 139.2 | 77.5 | 75.1 | 109.1 | ±17.3 |
| Posterior Trigeminal Nerve | 82.3 | 60.5 | 48.7 | 47.7 | X | 50.2 | 35.9 | 70.5 | 32.6 | 37.8 | 51.8 | ±5.5 |
| Olfactory Bulbs | 44.4 | 128.1 | 168.8 | 66.2 | 220.9 | 123.5 | 74.5 | 157.1 | 48.2 | 39.9 | 107.1 | ±19.6 |
| Anterior Olfactory Nucleus | 23.1 | 24.0 | 20.5 | 19.3 | 44.8 | 29.2 | 25.2 | 45.6 | 21.2 | 15.1 | 26.8 | ±3.3 |
| Frontal Cortex | 12.0 | 15.8 | 16.9 | 17.4 | 45.7 | 27.7 | 26.8 | 38.9 | 22.0 | 16.1 | 23.9 | ±3.5 |
| Parietal Cortex | 7.5 | 10.5 | 9.0 | 10.1 | 18.5 | 14.3 | 12.8 | 17.6 | 12.3 | 8.5 | 12.1 | ±1.2 |
| Temporal Cortex | 9.9 | 11.65 | 10.4 | 14.2 | 16.6 | 15.6 | 12.5 | 13.7 | 11.5 | 7.8 | 12.4 | ±0.9 |
| Occipital Cortex | 9.8 | 12.7 | 12.3 | 14.1 | X | 14.0 | 13.6 | 19.2 | 9.8 | 9.6 | 12.8 | ±1.0 |
| Extra Cortex | 10.3 | 12.40 | 13.3 | 13.8 | X | 17.2 | 12.8 | 16.6 | 9.8 | 11.3 | 13.0 | ±0.8 |
| Amygdala | 13.5 | 14.16 | 18.3 | 12.1 | 25.4 | 15.2 | 13.9 | 24.6 | 13.7 | 10.9 | 16.2 | ±1.6 |
| Striatum | 8.2 | 8.5 | 6.7 | 7.23 | 14.9 | 10.4 | 9.5 | 15.1 | 11.9 | 5.5 | 9.8 | ±1.0 |
| Septal Nucleus | 9.5 | 13.3 | 13.6 | 10.2 | 19.4 | 12.9 | 9.8 | X | 12.0 | 8.2 | 12.1 | ±1.1 |
| Hypothalamus | 17.1 | 21.1 | 15.8 | 17.4 | 37.6 | 28.8 | 15.7 | 38.9 | 17.3 | 11.9 | 22.2 | ±3.0 |
| Thalamus | 7.9 | 12.2 | 10.5 | 8.1 | 15.4 | 14.0 | 7.2 | 12.2 | 9.1 | 6.7 | 10.3 | ±1.0 |
| Midbrain | 12.3 | 13.1 | 15.3 | 10.0 | X | 15.9 | 9.9 | 16.4 | 9.9 | 9.5 | 12.5 | ±0.9 |
| Hippocampus | X | 11.6 | 10.6 | 8.8 | 16.4 | 13.4 | 7.0 | 13.7 | 8.2 | 7.0 | 10.7 | ±1.1 |
| Pons | 12.4 | 13.9 | 16.2 | 10.1 | 22.0 | 18.6 | 10.6 | 20.4 | 10.2 | 10.0 | 14.4 | ±1.5 |
| Medulla | 12.3 | 13.99 | 17.4 | 11.1 | 21.0 | 21.1 | 10.6 | 20.5 | 10.8 | 9.9 | 14.9 | ±1.5 |
| Cerebellum | 9.3 | 10.06 | 13.2 | 11.2 | X | 12.2 | 8.6 | 14.7 | 7.8 | 10.6 | 10.9 | ±0.7 |
| Extra Slice #1 | 17.1 | 19.4 | 16.6 | 16.9 | 43.2 | 31.1 | 29.6 | X | 22.7 | 16.2 | 23.6 | ±3.1 |
| Extra Slice #2 | 9.2 | 12.33 | 17.0 | 11.7 | 28.5 | 17.6 | 17.3 | 27.0 | 15.6 | 11.0 | 16.7 | ±2.1 |
| Extra Slice #3 | 8.8 | 11.43 | 10.7 | 9.9 | 23.3 | 17.2 | 13.6 | 21.0 | 13.8 | 9.6 | 13.9 | ±1.6 |
| Extra Slice #4 | 7.5 | 9.4 | 9.9 | X | 18.4 | 14.7 | 10.5 | 17.0 | 11.8 | 8.6 | 12.0 | ±1.3 |
| Extra Slice #5 | 7.7 | 10.7 | 9.2 | 10.8 | 19.2 | 18.6 | 9.7 | 14.8 | 9.9 | 7.6 | 11.8 | ±1.3 |
| Extra Slice #6 | 7.9 | 12.1 | 10.5 | 12.2 | X | 16.7 | 10.4 | 14.8 | 9.5 | 8.1 | 11.3 | ±1.0 |
| Pituitary | 86.9 | 58.9 | 51.8 | 79.3 | X | 59.7 | 44.3 | 67.9 | 48.1 | 44.0 | 60.1 | ±5.1 |
| Optic Chiasm | 20.7 | 41.3 | 34.7 | 51.4 | 8.4 | 38.2 | 27.0 | X | 28.7 | 14.4 | 29.4 | ±4.5 |
| Dorsal Dura | 116.0 | 118.2 | 156.9 | 116.8 | X | 131.0 | 132.9 | 242.5 | 89.5 | 92.5 | 132.9 | ±15.3 |
| Ventral Dura | 113.7 | 29.8 | 138.3 | 165.6 | 259.4 | 192.6 | 150.8 | 211.8 | 96.1 | 71.6 | 143.0 | ±21.7 |
| Spinal Dura | 23.1 | 36.1 | 21.4 | 16.9 | 26.6 | 26.2 | 39.7 | 20.1 | 29.5 | 26.3 | 26.6 | ±2.2 |

TABLE 1-continued

Intranasal kallikrien - nM concentrations - 30 min. end point-outliers removed

| | animal-1 | animal-2 | animal-3 | animal-4 | animal-5 | animal-6 | animal-13 | animal-14 | animal-15 | Animal-16 | Avg | SE |
|---|---|---|---|---|---|---|---|---|---|---|---|---|
| Upper Cervical Spinal Cord | 16.0 | 18.18 | 31.6 | 18.8 | 35.1 | 37.2 | 20.4 | 27.0 | 12.8 | 17.0 | 23.4 | ±2.7 |
| Lower Cervical Spinal Cord | 5.3 | 7.3 | 5.2 | 4.7 | 7.0 | 6.5 | 10.1 | 10.9 | 7.3 | 6.6 | 7.1 | ±0.6 |
| Thoracic Spinal Cord | 5.5 | 6.7 | 4.5 | 4.2 | 6.5 | 4.7 | 5.7 | 4.1 | 5.0 | 5.1 | 5.2 | ±0.3 |
| Lumbar Spinal Cord | 5.1 | 5.8 | 4.7 | 5.0 | 5.35 | 4.2 | 5.6 | 4.2 | 4.6 | 4.9 | 4.9 | ±0.2 |
| Circle of Willis & Basilar Artery | 190.7 | 44.4 | 133.6 | 87.4 | 178.2 | 115.5 | 44.1 | 134.1 | 48.3 | 56.9 | 103.3 | ±17.5 |
| Carotid Artery | 127.5 | 111.2 | 103.2 | X | 138.7 | 175.1 | 84.9 | 115.6 | 108.2 | 55.9 | 113.4 | ±11.1 |
| Renal artery (L) | 56.2 | 103.1 | 52.8 | 55.8 | 26.1 | 43.0 | 78.9 | 66.9 | 31.2 | 67.3 | 58.1 | ±7.2 |
| Superficial Nodes (2) | 58.8 | X | 42.2 | 60.1 | 66.8 | 69.0 | 94.2 | 68.0 | 68.0 | 39.9 | 63.1 | ±5.4 |
| Cervical Nodes (2) | 214.4 | 116.3 | 72.1 | 100.5 | 119.9 | X | 103.7 | 196.0 | 174.6 | 3.1 | 122.3 | ±21.8 |
| Axillary Nodes (2) | 44.6 | 58.8 | 44.4 | 43.9 | 48.8 | 28.6 | 33.5 | 47.7 | 34.0 | 38.9 | 42.3 | ±2.8 |
| Blood Sample | 292.4 | 327.7 | 288.9 | 275.6 | 231.1 | 233.0 | 251.9 | 242.4 | 268.4 | 272.4 | 268.4 | ±9.5 |
| Muscle (R, deltoid) | 24.2 | 24.2 | 17.5 | 15.8 | 12.4 | 16.5 | 23.1 | 29.3 | 33.2 | 17.7 | 21.4 | ±2.1 |
| Liver (R, superficial lobe) | 18.7 | 25.7 | 26.6 | 40.2 | 26.1 | 16.4 | 16.1 | 21.8 | 28.8 | 37.1 | 25.7 | ±2.6 |
| Kidney (L, tip) | 179.0 | 187.5 | 115.0 | 24.6 | 35.5 | 103.9 | 240.4 | 212.2 | 36.9 | 213.3 | 134.8 | ±26.0 |
| Urine | 249.2 | 190.9 | 57.8 | 51.1 | 65.6 | 287.4 | 95.8 | 139.2 | 90.6 | 79.5 | 130.7 | ±26.6 |
| Spleen (tip) | 29.0 | 35.1 | 87.5 | 91.1 | 82.9 | 75.4 | 89.8 | 73.8 | 80.0 | 81.5 | 72.6 | ±7.0 |
| Heart | 17.4 | 21.9 | 30.1 | 12.7 | 31.4 | 13.7 | 23.2 | 22.8 | 37.0 | 16.0 | 22.6 | ±2.6 |
| Lung (R, top lobe) | 48.6 | 46.8 | 18.2 | 37.2 | 30.1 | 27.9 | 24.4 | 64.3 | 25.5 | 48.7 | 37.2 | ±4.6 |
| Thyroid | 1,730.9 | 2,106.5 | 1,369.2 | 2,644.1 | 2,380.4 | 1,219.8 | 2,016.7 | 2,148.4 | 2,013.3 | 2,077.1 | 1970.6 | ±136.2 |
| Esophagus | 118.0 | 109.6 | 87.7 | 68.1 | 40.9 | 65.1 | 85.4 | 128.1 | 82.4 | 66.9 | 85.2 | ±8.5 |
| Trachea | X | 116.8 | 64.5 | 93.6 | 44.8 | 59.3 | 65.1 | 110.6 | 86.4 | 58.5 | 77.7 | ±8.4 |
| Drug Standard CPM | 5,493,399 | 5,493,399 | 5,338,245 | 5,338,245 | 5,298,640 | 5,298,640 | 4,686,179 | 4,686,179 | 5,097,205 | 5,097,205 | 5,182,734 | ±92,857.4 |
| Drug Standard CPM | 5,307,746 | 5,307,746 | 5,315,564 | 5,315,564 | 5,263,811 | 5,263,811 | 4,961,592 | 4,961,592 | 5,048,450 | 5,048,450 | 5,179,433 | ±48,700.2 |
| Drug Standard CPM | 5,299,464 | 5,299,464 | 5,397,460 | 5,397,460 | 5,345,835 | 5,345,835 | 4,945,669 | 4,945,669 | 4,934,899 | 4,934,899 | 5,184,665 | ±67,319.9 |

X = outliers removed

Example 8

Direct Cleavage of Soluble and Fibril Amyloid Beta

Amyloid beta$_{1-42}$ standard (from β-Amyloid$_{1-42}$ ELISA, Human kit, Sigma BE0200) was reconstituted into 1.0 μg/mL as per kit instructions. A stock solution of tissue kallikrein (SEQ ID: 1) and approximately 0.5 molar equivalents of Soybean Trypsin Inhibitor (Sigma, T6522) was prepared in PBS and serially diluted in triplicate with a fixed concentration of hAPβ42 peptide at 500 pg/mL.

Solutions were incubated for 3 and 18 hours respectively after which time additional protease inhibitors were added (1/100 dilution of protease inhibitor cocktail solution, Sigma P8340).

As per kit instructions, 50 μL of the above samples were added and the ELISA plate incubated overnight at 4° C. The remaining steps of the ELISA plate development were followed as per kit instructions and then read using a multiwell ELISA plate reader at 450 nm.

Percent cleavage was determined by:

$$100-[(\text{Ave KLK1}-\text{Ave Blank})/(\text{Ave Control}-\text{Ave Blank})\times 100]=\% \text{ Cleavage}$$

Results

TABLE 2

| | Percent Cleavage of Amyloid Beta by KLK1 | | | | | | |
|---|---|---|---|---|---|---|---|
| | 1 μg/mL | 100 ng/mL | 10 ng/mL | 1 ng/mL | 100 pg/mL | 10 pg/mL | 1 pg/mL |
| 3 hrs | 92.1% | 71.7% | 36.6% | 19.6% | 0% | 0% | 0% |
| 18 hrs | 100% | 99.8% | 88.4% | 50% | 19.5% | 15% | 0% |

Figure 17:
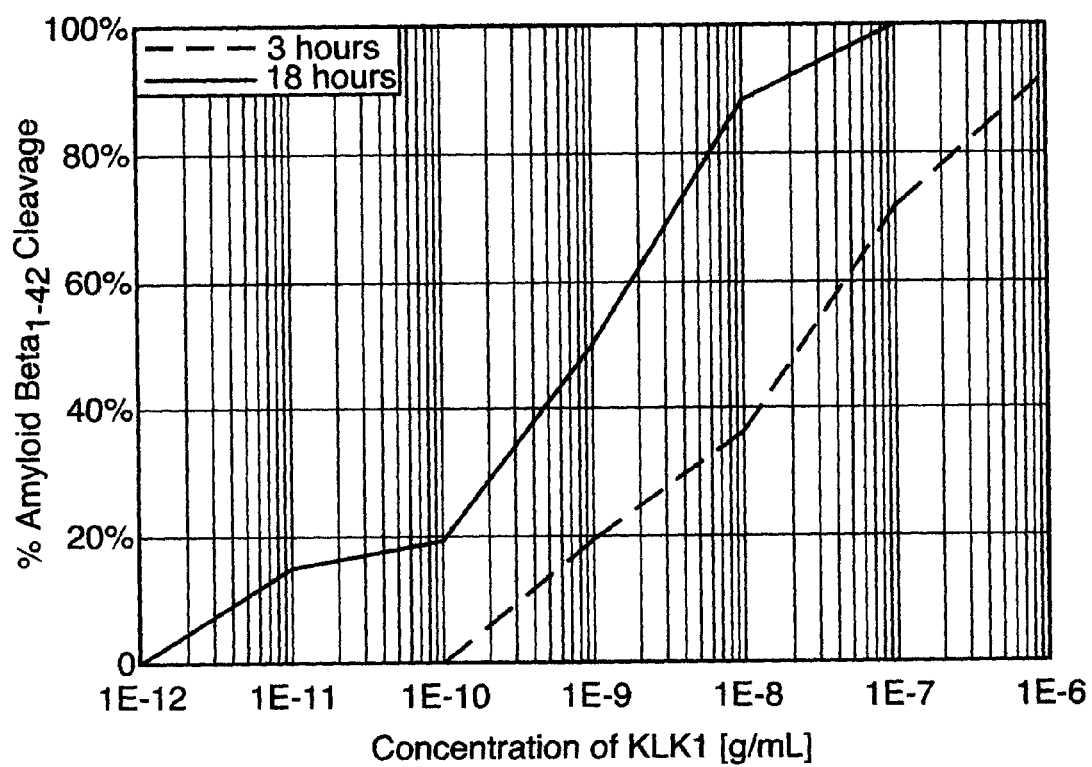
FIG. 17 is a logarithmic line graph showing the percentage of amyloid beta cleavage for various concentrations of tissue kallikrein.

The percentage of amyloid beta cleavage for various concentrations of KLK1 can be found in FIG. 17.

---

The invention claimed is:

1. A method of alleviating Alzheimer's disease or amnesic mild cognitive impairment in a patient, said method comprising administering to said patient a therapeutically effective amount of a tissue kallikrein-1 (KLK1) polypeptide, wherein the KLK1 polypeptide comprises an amino acid sequence at least 95% identical to residues 25-263 of SEQ ID NO:1 or residues 25-262 of SEQ ID NO:2.

2. The method according to claim 1, wherein the KLK1 polypeptide is administered concurrently with a second therapeutic compound useful in alleviating Alzheimer's disease or amnesic mild cognitive impairment.

3. The method of claim 2, wherein the second therapeutic compound comprises an acetylcholine precursor, a compound that enhances acetylcholine release, an acetylcholinesterase inhibitor, a muscarinic agonist, an antioxidant, an anti-inflammatory agent, a hormone, a calcium channel blocker, nerve growth factor, a nootropic agent, a neurotrophin small molecule mimetic, NMDA receptor antagonists, a 5-HT1A receptor agonist, an anti-amyloidogenic agent, an antihistamine, an ergoloid mesylate, ginkgo biloba, huperzine A, choline, lecithin, acetyl-l-carnitine, 4-aminopyridine, linopirdine, tacrine, rivastigmine, galantamine, metrifonate, eptastigmine, milameline, xanomeline, arecoline, oxotremorine, sabcomeline, talsaclidine, vitamin E, idebenone, co-enzyme Q10, n-acetyl cysteine, vitamin C, non-steroidal anti-inflammatory agent, estrogen, testosterone, or piracetam.

4. The method according to claim 1, wherein the KLK1 polypeptide is administered intranasally.

5. The method according to claim 4, wherein the therapeutically effective amount is about 0.001 to about 5000 International Units (IU) per day.

6. The method according to claim 1, wherein the KLK1 polypeptide is administered orally.

7. The method according to claim 6, wherein the therapeutically effective amount is about 0.001 to about 1000 IU per day.

8. The method of claim 1, comprising assessing improvement in neurovasculature in the brain of the patient.

9. The method of claim 1, comprising assessing improvement in oxygen uptake in the brain of the patient.

10. The method of claim 1, comprising assessing improvement in blood flow to the brain of the patient.

11. The method of claim 1, comprising assessing improvement in plaque clearance in the brain of the patient.

12. The method of claim 1, comprising assessing improvement in glucose uptake by the brain of the patient.

13. The method of claim 3, wherein the acetylcholinesterase inhibitor is donepezil.

* * * * *

SEQUENCE LISTING

<160> NUMBER OF SEQ ID NOS: 2

<210> SEQ ID NO 1
<211> LENGTH: 263
<212> TYPE: PRT
<213> ORGANISM: Sus scrofa

<400> SEQUENCE: 1

```
Met Trp Ser Leu Val Met Arg Leu Ala Leu Ser Leu Ala Gly Thr Gly
1               5                   10                  15

Ala Ala Pro Pro Ile Gln Ser Arg Ile Ile Gly Gly Arg Glu Cys Glu
            20                  25                  30

Lys Asp Ser His Pro Trp Gln Val Ala Ile Tyr His Tyr Ser Ser Phe
        35                  40                  45

Gln Cys Gly Gly Val Leu Val Asp Pro Lys Trp Val Leu Thr Ala Ala
    50                  55                  60

His Cys Lys Asn Asp Asn Tyr Gln Val Trp Leu Gly Arg His Asn Leu
65                  70                  75                  80

Phe Glu Asn Glu Val Thr Ala Gln Phe Phe Gly Val Thr Ala Asp Phe
                85                  90                  95

Pro His Pro Gly Phe Asn Leu Ser Leu Leu Lys Asn His Thr Lys Ala
            100                 105                 110

Asp Gly Lys Asp Tyr Ser His Asp Leu Met Leu Leu Arg Leu Gln Ser
        115                 120                 125

Pro Ala Lys Ile Thr Asp Ala Val Lys Val Leu Glu Leu Pro Thr Gln
    130                 135                 140

Glu Pro Glu Leu Gly Ser Thr Cys Gln Ala Ser Gly Trp Gly Ser Ile
145                 150                 155                 160

Glu Pro Gly Pro Asp Asp Phe Glu Phe Pro Asp Glu Ile Gln Cys Val
                165                 170                 175

Glu Leu Thr Leu Leu Gln Asn Thr Phe Cys Ala Asp Ala His Pro Asp
            180                 185                 190
```

```
Lys Val Thr Glu Ser Met Leu Cys Ala Gly Tyr Leu Pro Gly Gly Lys
            195                 200                 205

Asp Thr Cys Met Gly Asp Ser Gly Gly Pro Leu Ile Cys Asn Gly Met
    210                 215                 220

Trp Gln Gly Ile Thr Ser Trp Gly His Thr Pro Cys Gly Ser Ala Asn
225                 230                 235                 240

Lys Pro Ser Ile Tyr Thr Lys Leu Ile Phe Tyr Leu Asp Trp Ile Asn
                245                 250                 255

Asp Thr Ile Thr Glu Asn Pro
            260

<210> SEQ ID NO 2
<211> LENGTH: 262
<212> TYPE: PRT
<213> ORGANISM: Homo sapiens

<400> SEQUENCE: 2

Met Trp Phe Leu Val Leu Cys Leu Ala Leu Ser Leu Gly Gly Thr Gly
1               5                   10                  15

Ala Ala Pro Pro Ile Gln Ser Arg Ile Val Gly Gly Trp Glu Cys Glu
            20                  25                  30

Gln His Ser Gln Pro Trp Gln Ala Leu Tyr His Phe Ser Thr Phe
        35                  40                  45

Gln Cys Gly Gly Ile Leu Val His Arg Gln Trp Val Leu Thr Ala Ala
    50                  55                  60

His Cys Ile Ser Asp Asn Tyr Gln Leu Trp Leu Gly Arg His Asn Leu
65                  70                  75                  80

Phe Asp Asp Glu Asn Thr Ala Gln Phe Val His Val Ser Glu Ser Phe
                85                  90                  95

Pro His Pro Gly Phe Asn Met Ser Leu Leu Glu Asn His Thr Arg Gln
            100                 105                 110

Ala Asp Glu Asp Tyr Ser His Asp Leu Met Leu Leu Arg Leu Thr Glu
        115                 120                 125

Pro Ala Asp Thr Ile Thr Asp Ala Val Lys Val Val Glu Leu Pro Thr
    130                 135                 140

Glu Glu Pro Glu Val Gly Ser Thr Cys Leu Ala Ser Gly Trp Gly Ser
145                 150                 155                 160

Ile Glu Pro Glu Asn Phe Ser Phe Pro Asp Asp Leu Gln Cys Val Asp
                165                 170                 175

Leu Lys Ile Leu Pro Asn Asp Glu Cys Lys Lys Ala His Val Gln Lys
            180                 185                 190

Val Thr Asp Phe Met Leu Cys Val Gly His Leu Glu Gly Gly Lys Asp
        195                 200                 205

Thr Cys Val Gly Asp Ser Gly Gly Pro Leu Met Cys Asp Gly Val Leu
    210                 215                 220

Gln Gly Val Thr Ser Trp Gly Tyr Val Pro Cys Gly Thr Pro Asn Lys
225                 230                 235                 240

Pro Ser Val Ala Val Arg Val Leu Ser Tyr Val Lys Trp Ile Glu Asp
                245                 250                 255

Thr Ile Ala Glu Asn Ser
            260
```